US009265532B2

(12) United States Patent
Lamborne et al.

(10) Patent No.: US 9,265,532 B2
(45) Date of Patent: *Feb. 23, 2016

(54) INTERSPINOUS IMPLANTS AND METHODS

(75) Inventors: Andrew Lamborne, Golden, CO (US);
Justin Taber, Longmont, CO (US);
Michael Fulton, Superior, CO (US);
Joseph Maddux, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/854,125

(22) Filed: Aug. 10, 2010

(65) Prior Publication Data

US 2011/0166600 A1   Jul. 7, 2011

Related U.S. Application Data

(63) Continuation-in-part of application No. 12/538,710, filed on Aug. 10, 2009, which is a continuation-in-part of application No. 11/934,604, filed on Nov. 2, 2007.

(60) Provisional application No. 60/912,273, filed on Apr. 17, 2007, provisional application No. 60/884,581, filed on Jan. 11, 2007, provisional application No. 61/232,680, filed on Aug. 10, 2009.

(51) Int. Cl.
*A61B 17/70* (2006.01)
*A61B 17/82* (2006.01)

(52) U.S. Cl.
CPC ......... *A61B 17/7068* (2013.01); *A61B 17/7061* (2013.01); *A61B 17/82* (2013.01)

(58) Field of Classification Search
USPC ............... 606/246–249; 623/17.12–17.16, 623/17.111, 17.11
See application file for complete search history.

(56) References Cited

U.S. PATENT DOCUMENTS 5,496,318 A * 3/1996 Howland et al. .............. 606/249
5,645,599 A   7/1997 Samani
(Continued)

FOREIGN PATENT DOCUMENTS

CN    101129271 A    2/2008
JP    2003523214 A   8/2003
(Continued)

OTHER PUBLICATIONS

International Bureau, Notification Concerning Transmittal of International Preliminary Report on Patentability (Chapter I of the Patent Cooperation Treaty) May 14, 2010.
(Continued)

*Primary Examiner* — Jan Christopher Merene
(74) *Attorney, Agent, or Firm* — Schwegman Lundberg & Woessner, P.A.

(57) ABSTRACT

The present invention provides spinous process implant and associated methods. In one aspect of the invention the implant limits the maximum spacing between the spinous processes. In another aspect of the invention, a spacer has at least one transverse opening to facilitate tissue in-growth. In another aspect of the invention, an implant includes a spacer and separate extensions engageable with the spacer. The spacer is provided in a variety of lengths and superior to inferior surface spacings. In another aspect of the invention, an implant includes a spacer and a cerclage element offset from the midline of the spacer in use so that the spacer defines a fulcrum and the cerclage element is operative to impart a moment to the vertebrae about the spacer. In another aspect of the invention, instrumentation for inserting the implant is provided. In other aspects of the invention, methods for treating spine disease are provided.

28 Claims, 31 Drawing Sheets

(56) References Cited

U.S. PATENT DOCUMENTS

| | | | |
|---|---|---|---|
| 6,190,387 B1* | 2/2001 | Zucherman et al. | 606/249 |
| 7,048,736 B2* | 5/2006 | Robinson et al. | 606/86 B |
| 7,201,751 B2 | 4/2007 | Zucherman et al. | |
| 7,658,752 B2 | 2/2010 | Labrom et al. | |
| 7,871,426 B2* | 1/2011 | Chin et al. | 606/248 |
| 7,922,750 B2 | 4/2011 | Trautwein et al. | |
| 7,955,392 B2* | 6/2011 | Dewey et al. | 623/17.16 |
| 8,167,915 B2 | 5/2012 | Ferree et al. | |
| 2001/0021851 A1* | 9/2001 | Eberlein et al. | 606/69 |
| 2002/0045899 A1* | 4/2002 | Errico et al. | 606/61 |
| 2002/0116000 A1* | 8/2002 | Zucherman et al. | 606/61 |
| 2002/0183746 A1 | 12/2002 | Zucherman et al. | |
| 2003/0040746 A1 | 2/2003 | Mitchell et al. | |
| 2003/0153912 A1* | 8/2003 | Graf | 606/61 |
| 2004/0153071 A1* | 8/2004 | Zucherman et al. | 606/61 |
| 2005/0192574 A1 | 9/2005 | Blain | |
| 2005/0203512 A1 | 9/2005 | Hawkins et al. | |
| 2006/0015181 A1* | 1/2006 | Elberg | 623/16.11 |
| 2006/0064166 A1* | 3/2006 | Zucherman et al. | 623/17.11 |
| 2006/0235400 A1* | 10/2006 | Schneider | 606/69 |
| 2006/0247640 A1* | 11/2006 | Blackwell et al. | 606/71 |
| 2006/0264938 A1 | 11/2006 | Zucherman | |
| 2006/0271194 A1* | 11/2006 | Zucherman et al. | 623/17.11 |
| 2007/0093825 A1 | 4/2007 | Ferree et al. | |
| 2007/0142915 A1 | 6/2007 | Altarac et al. | |
| 2007/0225706 A1 | 9/2007 | Clark et al. | |
| 2008/0147190 A1 | 6/2008 | Dewey et al. | |
| 2008/0147192 A1 | 6/2008 | Edidin et al. | |
| 2008/0312741 A1 | 12/2008 | Lee et al. | |
| 2010/0036419 A1 | 2/2010 | Patel et al. | |
| 2010/0222817 A1 | 9/2010 | Perez-Cruet et al. | |

FOREIGN PATENT DOCUMENTS

| | | |
|---|---|---|
| KR | 20060124851 A | 12/2006 |
| WO | WO-03099147 A1 | 12/2003 |
| WO | WO-2004039239 A2 | 5/2004 |
| WO | WO-2005055868 A2 | 6/2005 |
| WO | WO-2007019391 A2 | 2/2007 |
| WO | WO-2008067452 A1 | 6/2008 |
| WO | WO-2008088613 A2 | 7/2008 |

OTHER PUBLICATIONS

European Search Report for European Patent Application No. 10759359.2, issued by the European Patent Office on Nov. 26, 2013. 6 pages.

Notice of Reasons for Rejection (English Translation) for Japanese Patent Application No. 2010-532090, issued by the Japan Patent Office on Sep. 24, 2013. 3 pages.

European Search Report for European Patent Application No. 13180855.2, issued by the European Patent Office on Oct. 7, 2013. 4 pages.

Defendant Pioneer Surgical Technology, Inc.'s Invalidity Contentions filed Jul. 31, 2013 in the U.S. District Court for the District of Colorado, Civil Action No. 1:13-cv-01035-WJM-BNB, 27 pages.

* cited by examiner

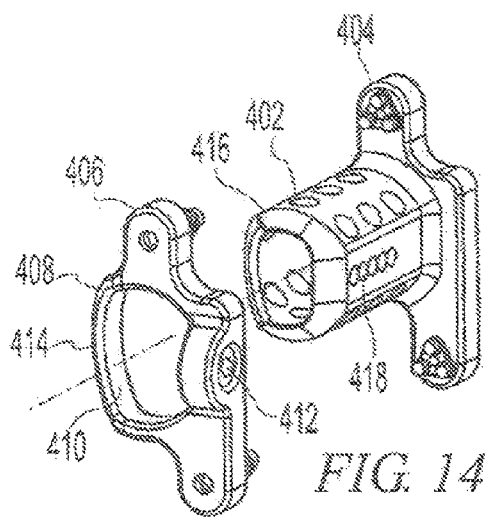
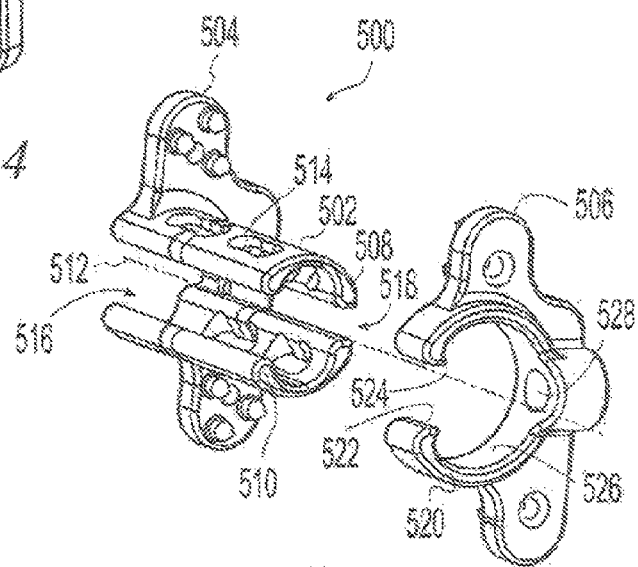
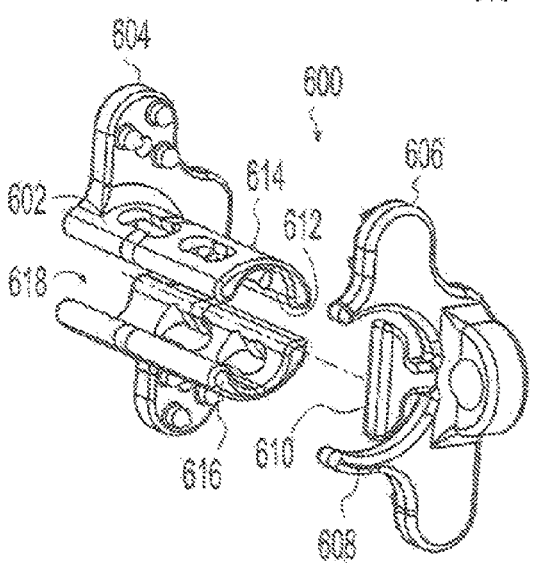
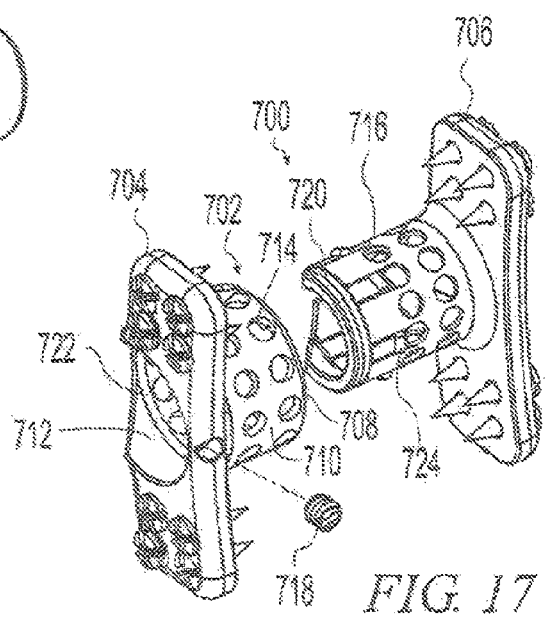

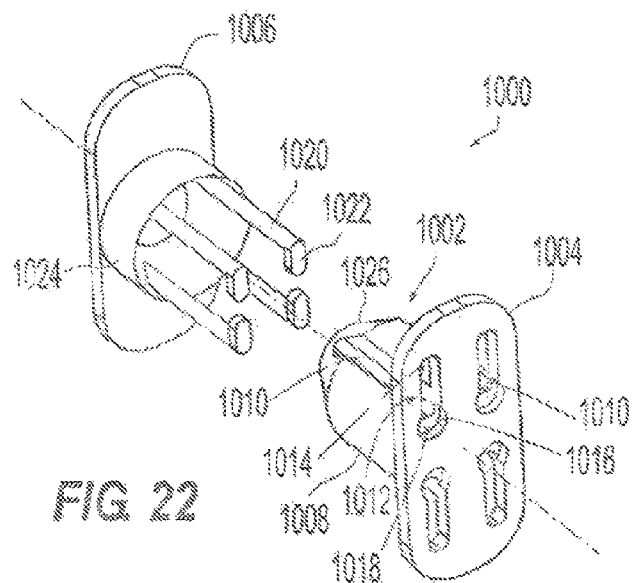
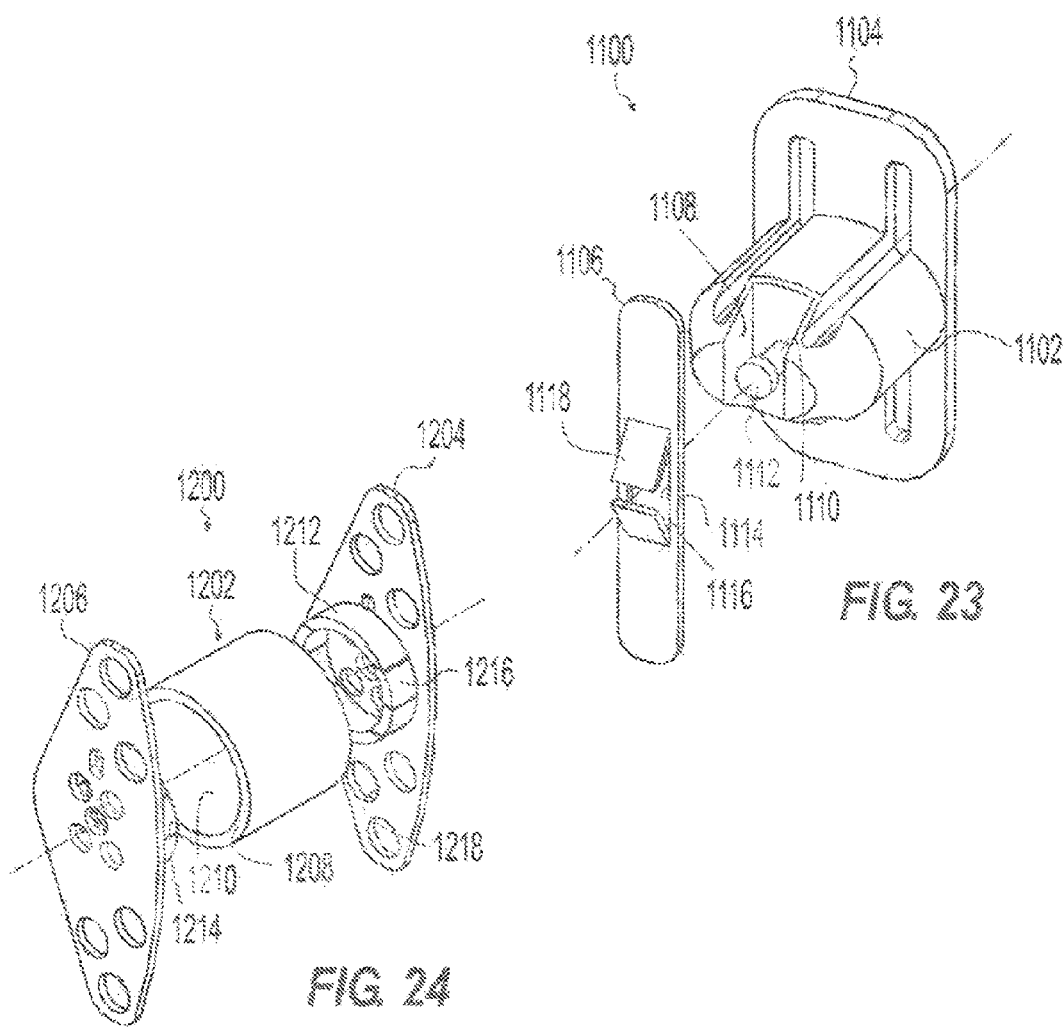

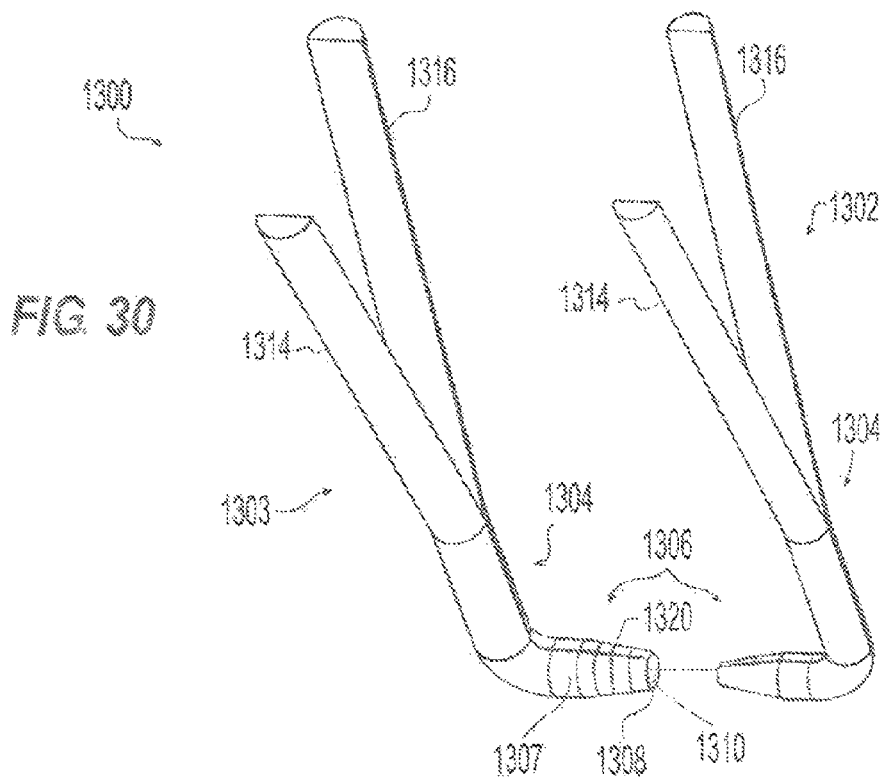
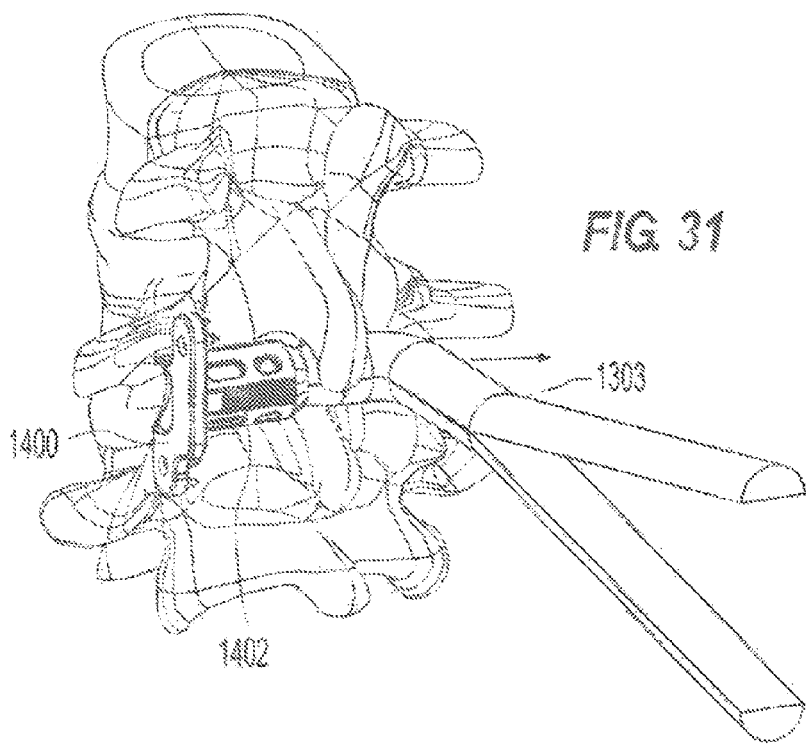

INTERSPINOUS IMPLANTS AND METHODS

CROSS-REFERENCE TO RELATED APPLICATIONS

This application is a continuation-in-part of U.S. patent application Ser. No. 12/538,710, filed Aug. 10, 2009, which is a continuation-in-part of U.S. patent application Ser. No. 11/934,604, filed Nov. 2, 2007, which claims the benefit of U.S. Provisional Patent Application No. 60/912,273, filed Apr. 17, 2007, and U.S. Provisional Application No. 60/884,581, filed Jan. 11, 2007, all of which are hereby incorporated by reference in their entirety.

This application claims the benefit of U.S. Provisional Patent Application No. 61/232,680, filed Aug. 10, 2009.

FIELD

The present disclosure relates to spinous process implants and associated instruments and methods.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age, spinal discs begin to break down, or degenerate resulting in the loss of fluid in the discs, and consequently, the discs become less flexible. Likewise, the discs become thinner allowing the vertebrae to move closer together. Degeneration also may result in tears or cracks in the outer layer, nr annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to deride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

More recently, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed.

BRIEF DESCRIPTION OF THE DRAWINGS

Various examples of the present invention will be discussed with reference to the appended drawings. These drawings depict only illustrative examples of the invention and are not to be considered limiting of its scope.

FIGS. 14-24 are perspective views of alternative embodiments of a spinous process implant;

FIG. 30 is a perspective view of instrumentation for implanting implants like those of FIGS. 1-29;

FIG. 31 is a perspective view of the instrumentation of FIG. 30 in use to implant the implant of FIG. 1 during an implantation procedure;

DESCRIPTION OF THE ILLUSTRATIVE EXAMPLES

Figure 1:
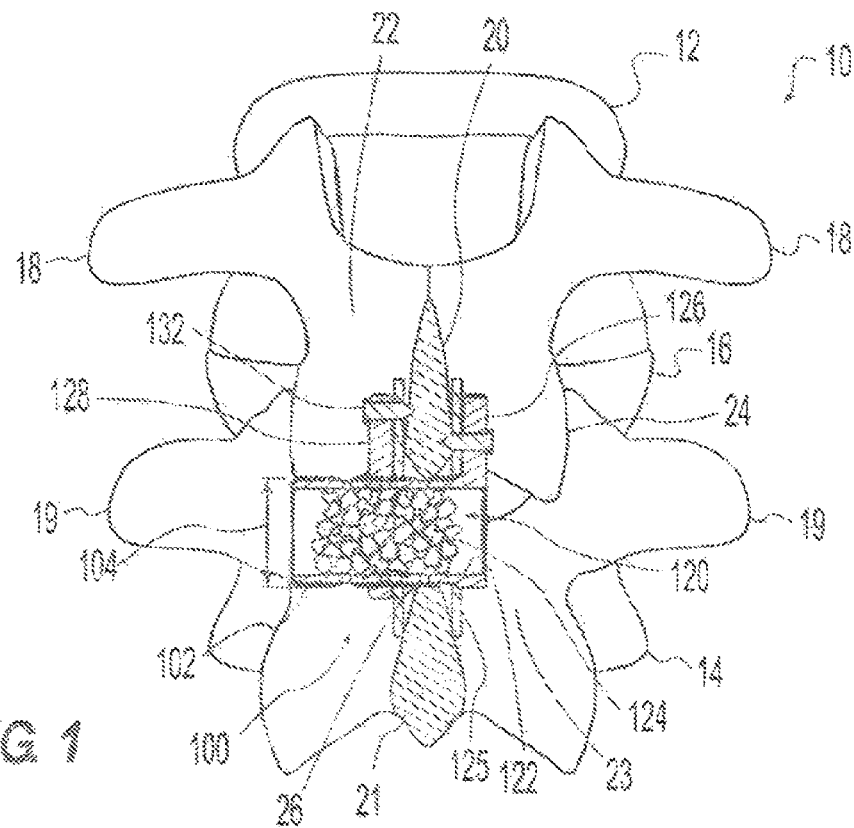
FIG. 1 is a posterior cross sectional view of an implant according to the present invention in situ.

Embodiments of spinous process implants according to the present invention include a spacer and an extension extending outwardly from the spacer. The extension is sometimes described as being one or more lobes associated with the spacer. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances.

The spacer may have any suitable cross-sectional shape. For example, it may be cylindrical, D-shaped, C-shaped, H-shaped, include separated cantilevered beams, and/or any other suitable shape. The shape may include chamfers, fillets, flats, relief cuts, and/or other features to accommodate anatomical features such as for example the lamina and/or facets.

The extension may extend transversely from the spacer relative to a spacer longitudinal axis to maintain the spacer between adjacent spinous processes. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is movable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material.

Cerclage may be used to stabilize the spinous process implant and/or to provide other benefits. For example, wires, straps, bands, cables, cords, and/or other elongated members may encircle the pedicles, lamina, spinous processes, transverse processes, and/or other spinal structures. The cerclage may be relatively inextensible to provide a hard check to spine flexion or the cerclage may be relatively extensible to provide increasing resistance to flexion. The cerclage may be relatively flexible and trappable such as a woven fabric or it may be relatively rigid such as a metal band. The cerclage may have shape memory properties that cause it to resume a prior set shape after implantation. The cerclage may be independent of the spinous process implant or may engage it. For example, the cerclage may pass through a hollow interior of the spinous process implant and/or engage the extension. The cerclage may be offset from the spacer and provide a tensioning force that uses the spacer as a fulcrum to offload the disc and/or open the disc space.

The implant may be supplemented with bone growth promoting substances to facilitate fusion of adjacent vertebrae between spinous processes, lamina, transverse processes, facets, and/or other spinal structures. The bone growth promoting substances may be spaced from the implant, placed adjacent the implant, sandwiched between the implant and underlying bone, placed inside the implant, coated onto the implant, and/or otherwise placed relative to the implant. If it is coated onto the implant it may cover the entire implant or only selected portions of the implant such as the extensions, fasteners, spinous process contacting portions of the spacer, and/or other portions.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, other suitable bone growth promoting substances, and/or combinations thereof.

The implant and any associated cerclage or other components may be made of any suitable biocompatible material including among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluoropolymers, and/or other suitable biocompatible materials and combinations thereof.

The spinous process implant may be used to treat spine disease in a variety of surgical techniques including superspinous ligament sacrificing posterior approaches, superspinous ligament preserving posterior approaches, lateral approaches, and/or other suitable approaches. The spinous process implant may be used to treat spine disease by fusing adjacent vertebrae or by preserving motion between adjacent vertebrae. It may include only an extension stop such as a spacer, only a flexion stop such as flexible cerclage elements, or both a flexion and extension stop, such as spinous process fasteners. The spinous process implant may be used to reduce loads on the facet joints, increase spinous process spacing, reduce loads on the disc, increase anterior disc spacing, and/or otherwise treat spine disease. Anterior effects may be accomplished by tensioning spine elements posterior to the spacer to apply a mechanical advantage to the spinal construct. Techniques for the spinal process implant may include leaving the tissues at the surgical site unmodified or modifying tissues such as trimming, rasping, roughening, and/or otherwise modifying tissues at the implant site.

The spinous process implant may have a dimension in a first direction that is less than a dimension in a second direction to aid in inserting the spinous process implant between adjacent spinous processes. For example, the spinous process implant may have a longitudinal axis and a leading end near one end of the longitudinal axis. The leading end may have a first dimension transverse to the longitudinal axis that is less than a second dimension transverse to the longitudinal axis such that the spinous process implant may be oriented with the first dimension aligned with the space between adjacent spinous processes to ease insertion and then oriented with the second dimension aligned with the spinous processes to space them apart a distance equal to the second dimension.

Insertion of spinous process implants may be facilitated by a set of instruments alternately engageable with one another to increase the interspinous space and engageable with a spinous process implant to help maneuver it between adjacent spinous processes.

Insertion of spinous process implants may be facilitated by an introducer insertable between adjacent spinous processes and able to engage a spinous process implant to help maneuver it between the adjacent spinous processes. The introducer may be rigid, flexible, or include both rigid and flexible portions. The introducer may engage the inside and/or the outside of the spinous process implant. The introducer may engage a relatively small portion or a relatively large portion of the spinous process implant. For example, the introducer may include a sleeve and/or trocar engageable with the inside or outside of the spinous process implant in nesting relationship. For example, a rigid sleeve may be positioned between adjacent spinous processes and then receive a spinous process implant such that when the sleeve is withdrawn the implant remains between the spinous processes. Such a sleeve may be initially inserted by installing a trocar in the sleeve. The introducer may include a flexible leader that is threadable between adjacent spinous processes to then draw the introducer and/or spinous process implant between the spinous processes. For example the introducer may include a sleeve with a relatively small diameter flexible leader extending from a first end and may be engageable with a spinous process implant at a second end such that it may be assembled with a spinous process implant and then the assembly drawn between the spinous processes by pulling on the leader. Alternatively, the introducer may be drawn between the spinous processes and then joined with the implant. The sleeve may be flexible to resiliently couple to the spinous process implant such as by compressing inside of the implant and/or stretching around the outside of the implant. The introducer may be solid or hollow. It may be rigid or flexible. It may be made of metal, plastic, and/or other suitable materials. The introducer may loosely engage the spinous process implant, as in a sliding relationship, or it may engage the spinous process implant such that the implant is constrained to move with the introducer. The introducer may engage the spinous process implant via a friction fit or a positive engagement.

Figure 2:
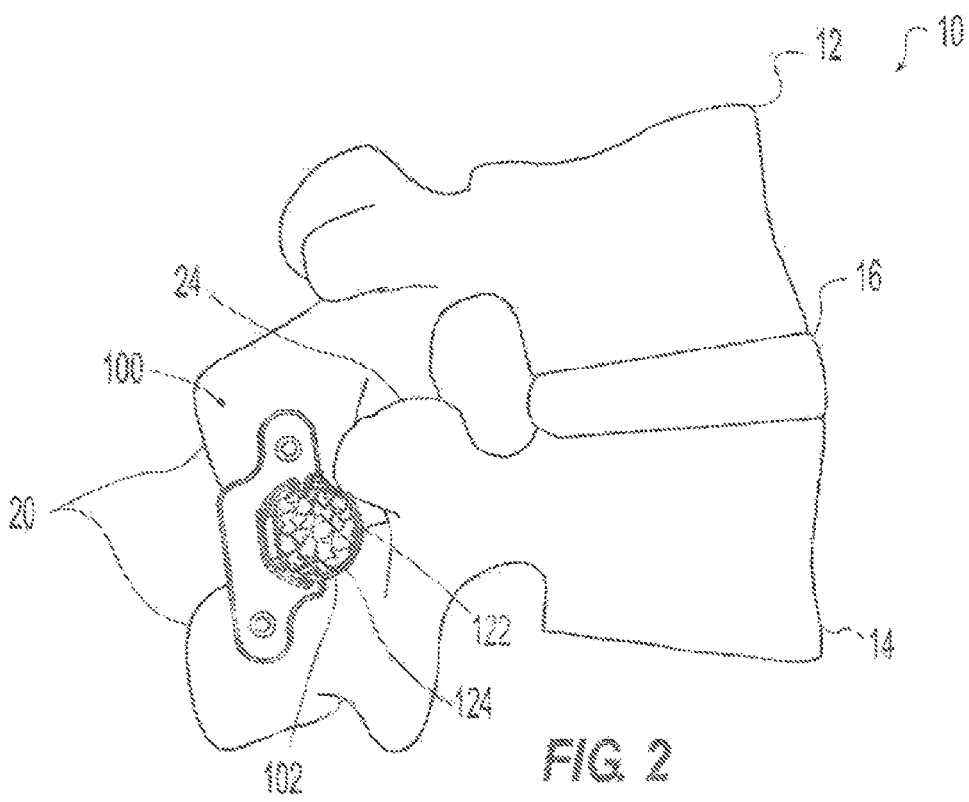
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The geometry of the implant 100 is illustrated with the use of axes that define length (l), height (h), and width (w) directions for the spacer.

When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of lacer 102 limits how closely the spinous processes 20, 21 can move together. Thus, the spacer 102 maintains a minimum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
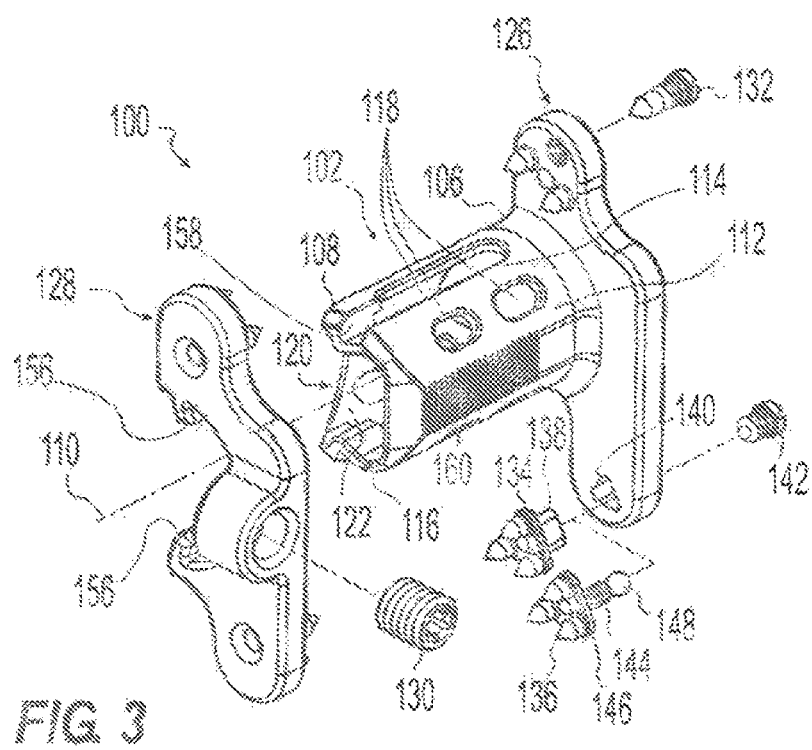
FIG. 3 is a an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. The extensions 126, 128 preferably extend inferiorly as well as superiorly from spacer 102 to optionally attach to the inferior spinous processes to immobilize the spinous processes 20, 21 relative to one another while fusion takes place.

Fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured such as by screw 142 to adjust the tension in the joint and/or to lock the fastener 136 in a predetermined orientation.

Figure 4:
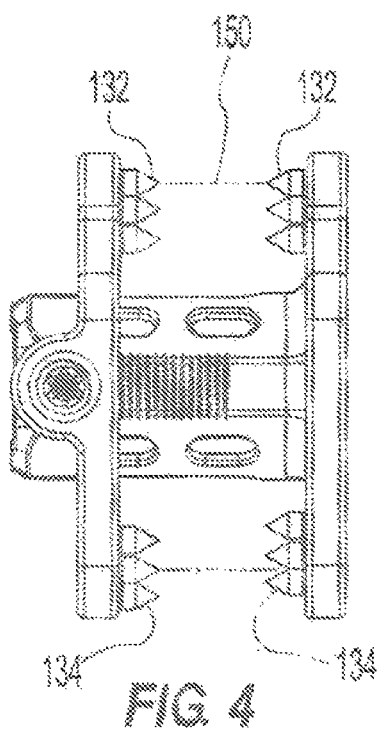
FIG. 4 is a posterior elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave if necessary as they are pressed into a bone. Any combination of fastener type, number, and alignment may be provided on the implant 100.

Figure 5:
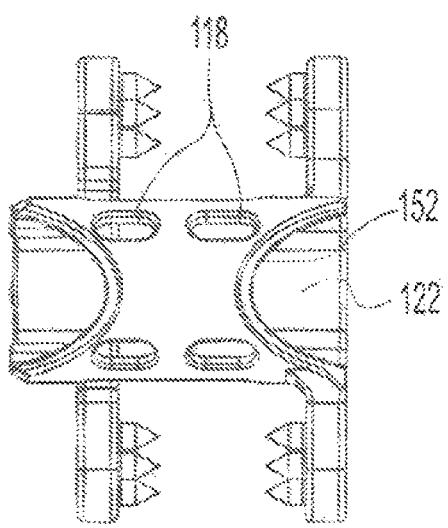
FIG. 5 is an anterior elevational view of the implant of FIG. 1.
Figure 6:
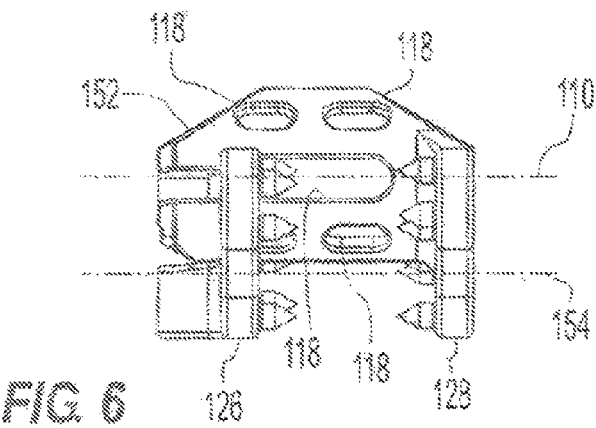
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
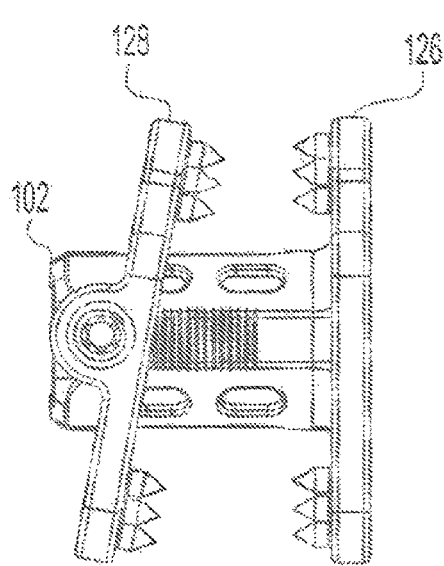
FIG. 7 is a posterior elevational view of the implant of FIG. 1 showing the assembly in an alternate position.
Figure 8:
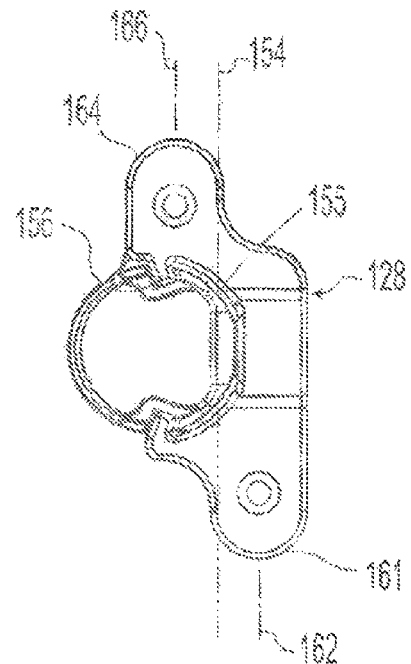
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally along the spacer length l toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
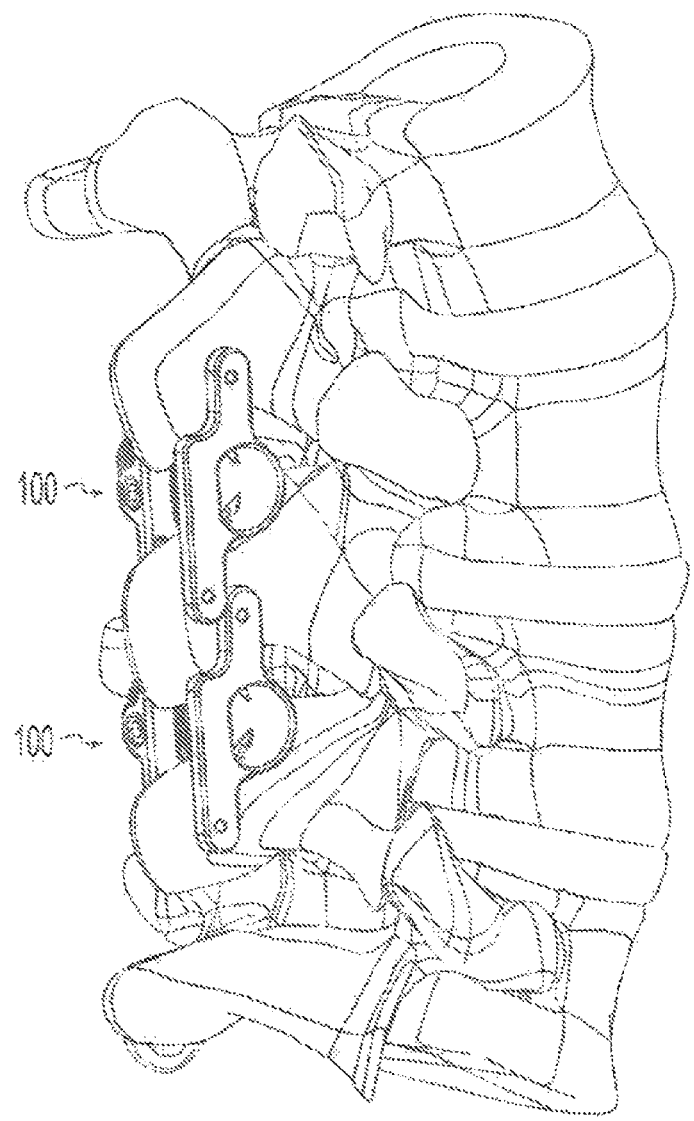
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface radius $r_4$, while second superior lobe radius $r_3$ is substantially equal to inferior concave surface radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition, the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162, 166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

Figure 10:
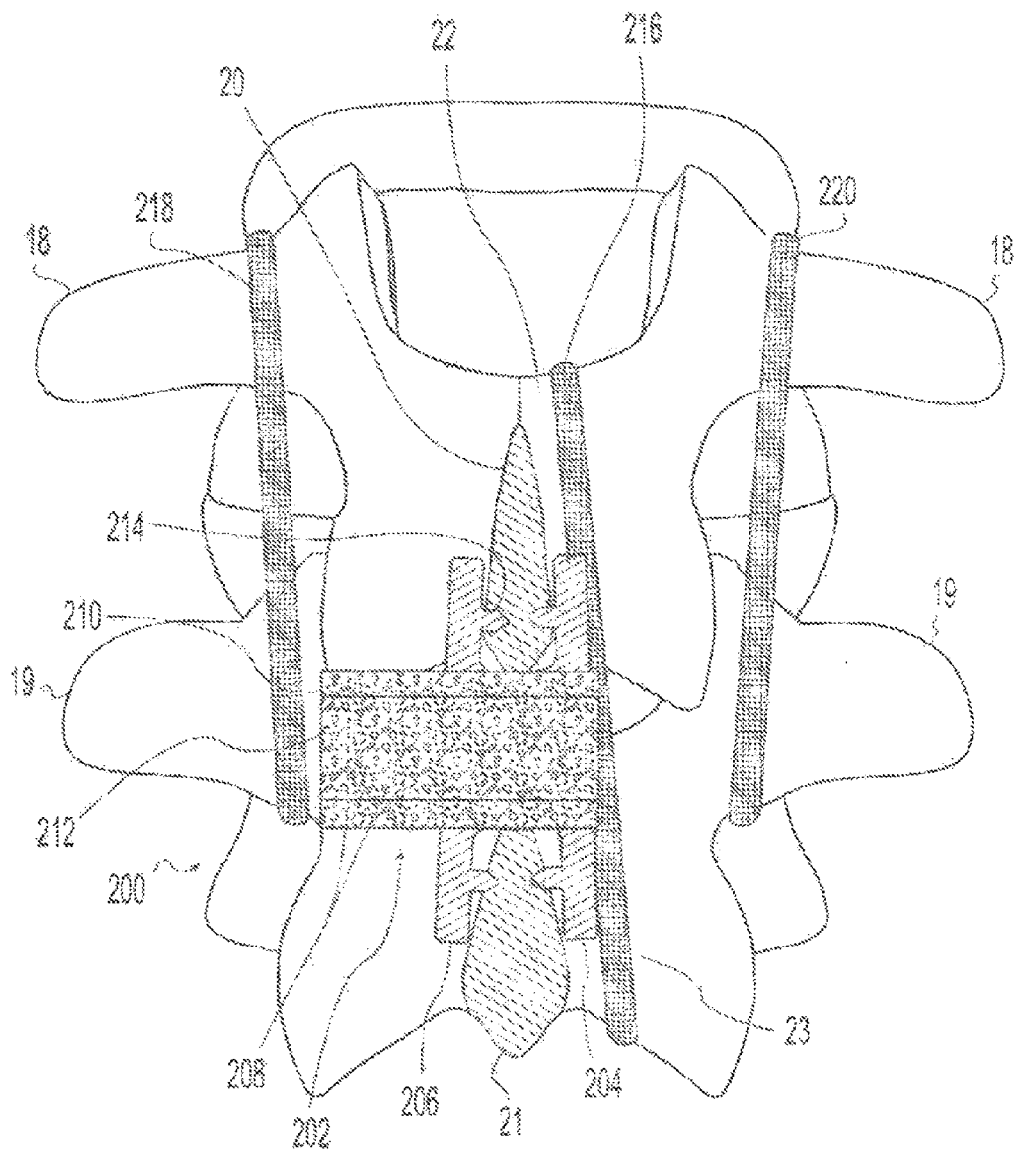
FIG. 10 is a posterior cross sectional view of an implant like that of FIG. 1 illustrating an alternate material and cerclage elements.

FIG. 10 depicts an implant 200 having a spacer 202 and first and second extensions 204, 206. The spacer 202 includes pores 208 to allow tissue to grow. The pores 208 may be individual openings spaced from one another, interconnecting openings, or combinations of individual and interconnecting openings. The spacer 202 may be a monolithic block having uniform porosity throughout. Alternatively, the spacer 202 may include an outer porous layer 210 and an inner layer 212 of different composition. For example, the inner layer 212 may be solid, porous, hollow, or some other configuration. A porous inner layer may have pores of a different size and/or distribution than the outer layer 210. Similarly, any porous portion may have uniform porosity or porosity that varies in pore size or density. A variety of pore configurations are suitable. Preferably the pore size is in the range of from about 1 µm to about 2 mm. More preferably, the pore size is in the range of from about 1 µm to about 500 µm. Still more preferably, the pore size is in the range of from about 75 µm to about 300 µm. The pores may be produced by a variety of processes such as sintering of particles; leaching a soluble component from the material; matting, weaving, or otherwise combining fibers; and/or by any other known process. The pore size may be tailored to preferentially promote hard tissue growth, soft tissue growth, or a combination of hard and soft tissue growth. The extensions 204, 206 may be solid or they may have large and/or small openings to encourage bone growth in and/or around the extensions 204, 206. The spacer 202 and/or extensions 204, 206 also may be coated as previously described.

The extensions 204, 206 may be fixed and/or adjustable. In the illustrative implant 200 of FIG. 10, the first extension 204 is fixed to one end of the spacer 202 and the second extension 206 is translatable along the length of spacer 202 to allow the extensions to be placed adjacent the spinous processes. The extensions 204, 206 are shown with optional fasteners, e.g., spikes 214 that may engage the spinous processes 20, 21 to fix the spinous processes 20, 21 relative to one another.

FIG. 10 also depicts the use of cerclage in conjunction with the implant 200. For example, one or more flexible bands 216 are placed around the lamina 22, 23 to provide a flexion stop. The band 216 may help carry the load exerted on the spikes 214 during spine flexion. Alternatively or in addition to the band 216, one or more bands 218, 220 may be placed around the transverse processes 18, 19.

Figure 11:
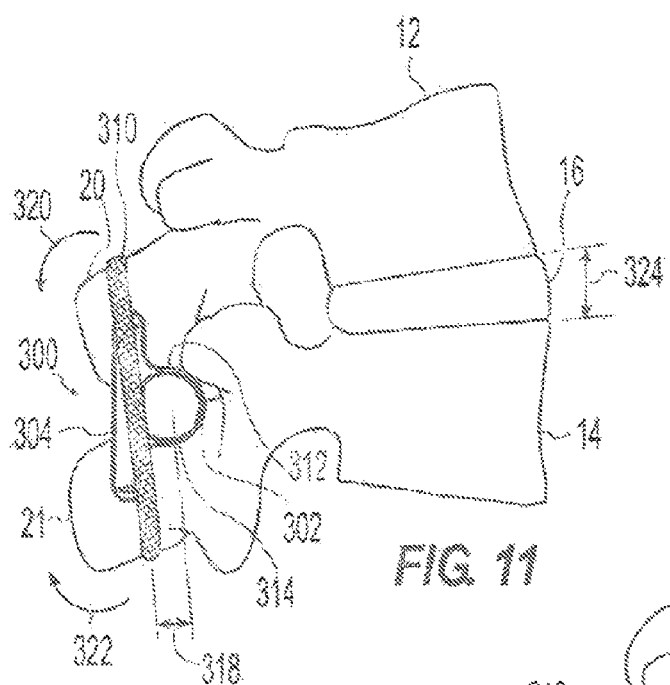
FIGS. 11-13 are side elevational views of an implant like that of FIG. 1 shown in use with cerclage elements.
Figure 12:
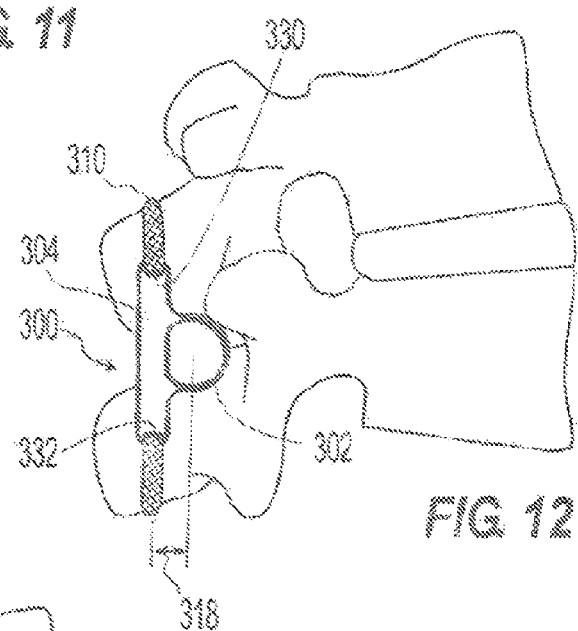
Figure 13:
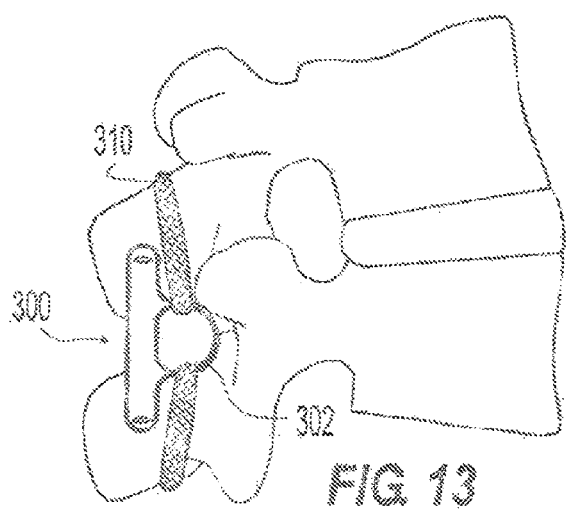

FIGS. 11-13 depict additional examples of the use of cerclage in conjunction with a spinous process implant 300 according to the present disclosure. The implant includes a spacer 302 for placement between adjacent spinous processes 20, 21 and an extension 304. In the example of FIG. 11, a band 310 of flexible material is looped around the spinous processes 20, 21. By placing the band 310 behind the areas 312, 314 where the spinous processes contact the spacer 302 an offset 318 is created. Tightening of the band 310 creates a moment 320, 322 on each vertebra 12, 14 that offloads some of the pressure on the disc 16 between the adjacent vertebrae 12, 14. With increased tightening of the band 310, the anterior spacing 324 of the vertebrae 12, 14 may actually be increased. Thus, by using the spinous process implant 300 in combination with the band 310, the vertebrae 12, 14 may be levered apart with the implant 300 being used as the fulcrum. In addition to the advantages already mentioned, this combination produces an anterior disc space effect with a posterior spinous process procedure that is less invasive than typical disc spacing procedures.

In the examples of FIGS. 12 and 13, the implant 300 includes a mechanism for attaching the cerclage band 310 to the implant 300. In the example of FIG. 12, the mechanism includes openings 330, 332 in the superior and inferior ends of the extension 304. By attaching the band 310 to the extension 304, the band 310 and extension 304 help stabilize one another against anterior-posterior displacement. This attachment also helps position the band 310 at a predetermined offset 318 from the spacer 302. In the example of FIG. 13, the band 310 is looped through a hollow interior of the spacer 302 itself. In this example, the band is not offset and produces minimal or no moment on the vertebrae.

FIGS. 14-24 illustrate alternative mechanisms for attaching a movable extension to the implant of FIG. 1. Referring to FIG. 14, an implant 400 includes a spacer 402, a first extension 404 and a second, movable extension 406. The movable extension 406 includes a body in the form of a ring 408 with an inner surface 410 generally conforming to the outer surface of the spacer 402 so that the ring is slidingly receivable on the spacer 402. A set screw 412 is tightened against the spacer 402 to fix the movable extension 406 at a desired position on the spacer 402. Tightening of the set screw 412 biases the movable extension 406 posteriorly relative to the spacer 402. The anterior portion 414 of the ring presses against the anterior portion 416 of the spacer 402 to counter this posterior bias and allow the set screw 412 to lock the movable extension 406. The spacer 402 may include a plurality of indentations 418 to create a positive engagement with the set screw 412 at predetermined axial locations. The ring 408 may be sized to permit a predetermined amount of tilting of the movable extension 406 relative to the spacer 402.

Referring to FIG. 15, an implant 500 includes a spacer 502, a first extension 504, and a second, movable extension 506. The spacer 502 includes a plurality of cantilevered beams 508, 510 projecting parallel to a longitudinal axis 512 away from the first extension 504. In the example of FIG. 15, the spacer 502 includes a pair of opposed "C"-shaped beams 508, 510 with their concave surfaces facing inwardly. The spacer 502 includes openings 514 through the beams 508, 510 and defines elongated openings 516, 518 anteriorly and posteriorly between the beams. The movable extension 506 includes a body in the form of an interrupted ring 520. The ring 520 is open anteriorly and the margins of the opening define posteriorly directed hooks 522, 524. The inner surface 526 of the ring conforms generally to the outer surface of the beams 508, 510 so that the ring is slidingly receivable on the spacer 502. The open anterior configuration of the ring 520 provides clearance to ease sliding of the ring in-vivo. A set screw 528 is tightened against the spacer 502 to fix the movable extension 506 at a desired longitudinal position on the spacer. The hooks 522, 524 curve around a portion of the anterior edge of the beams 508, 510 to resist posterior translation of the ring relative to the spacer 502 when the set screw 528 is tightened.

Referring to FIG. 16, an implant 600 is depicted that is similar to implant 500 of FIG. 15 having a spacer 602, first extension 604, and movable extension 606. However, the ring 608 is truncated anteriorly to provide even more anterior clearance than the ring 520 of FIG. 15. The ring 608 includes a key 610 projecting anteriorly from the posterior side of the ring 608 and expanding superiorly and inferiorly to engage the inner surface 612 of the beams 614, 616 to resist posterior translation of the ring relative to the spacer 602. The key 610 also partially blocks the hollow interior 618 of the spacer 602 to help retain material optionally packed into the interior 618.

Referring to FIG. 17, an implant 700 includes a spacer 702, a first extension 704, and a second movable extension 706. The spacer 702 includes a sidewall 708 defining an outer surface 710 and an inner surface 712. In the example of FIG. 17, the spacer 702 is generally in the shape of a hollow flattened cylinder with a "D"-shaped cross section. However, the spacer 702 could be any desirable shape. The spacer 702 includes a plurality of openings 714 communicating from the outer surface 710 to the inner surface 712. The movable extension 706 includes a projection 716 configured generally like the spacer 702 but being sized to slide within the spacer 702 in telescoping relationship. The projection (or the spacer) may optionally include one or more fixation mechanisms to lock the extensions 704, 706 at a desired longitudinal spacing. Fixation mechanisms may include a set screw 718, a ridge 720 forming a snap fit with a groove 722 or other feature, a detent 724 engageable with openings 714, and/or other suitable fixation mechanisms. Any one or combinations of these mechanisms may be used and they may be reversed from the orientation shown.

Figure 18:
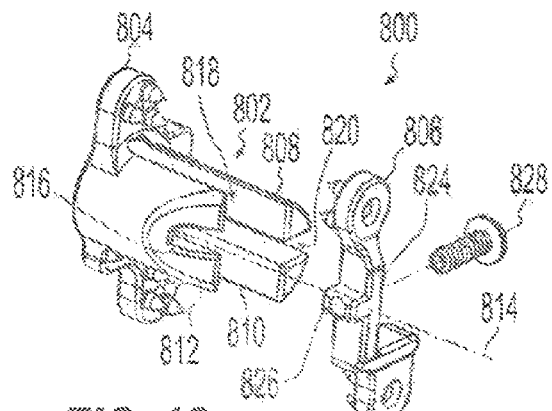
Figure 19:
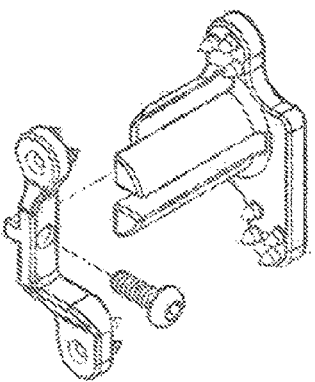
Figure 20:
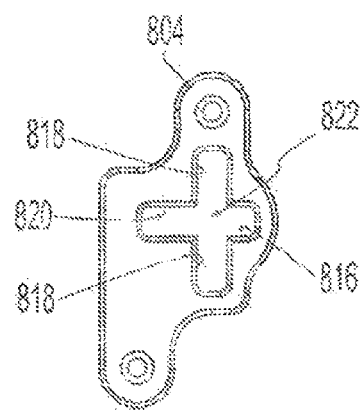

Referring to FIGS. 18-20, an implant 800 includes a spacer 802, a first extension 804, and a second, movable extension 806. The spacer 802 includes a plurality of cantilevered beams similar to FIGS. 15 and 16 except that in this example there are three beams 808, 810, 812. The beams project parallel to a longitudinal axis 814 away from the first extension 804. In the example of FIG. 18, the anterior beam 812 includes a posteriorly opening groove 816. The posterior beams 808, 810 and anterior beam 812 define an elongated slot 818 between them opening superiorly and inferiorly. The posterior beams 808, 810 further define an elongated slot 820 between them opening posteriorly. FIG. 20 illustrates a cruciform opening 822 defined by the projection of the groove 816 and slots 818, 820 projected through the first extension 804. The movable extension 806 includes a body 824 sized to slidingly engage the slot 818. An optional lug 826 can project anteriorly into groove 816 to constrain tilting of the movable extension 806 relative to the first extension 804. The lug 826 can be sized to fit closely within groove 816 to prevent tilting of the movable extension 806 or it can be sized smaller than the groove 816 to permit a predetermined amount of tilt. A set screw 828 is provided to lock the movable extension 806 to the spacer 802.

Figure 21:
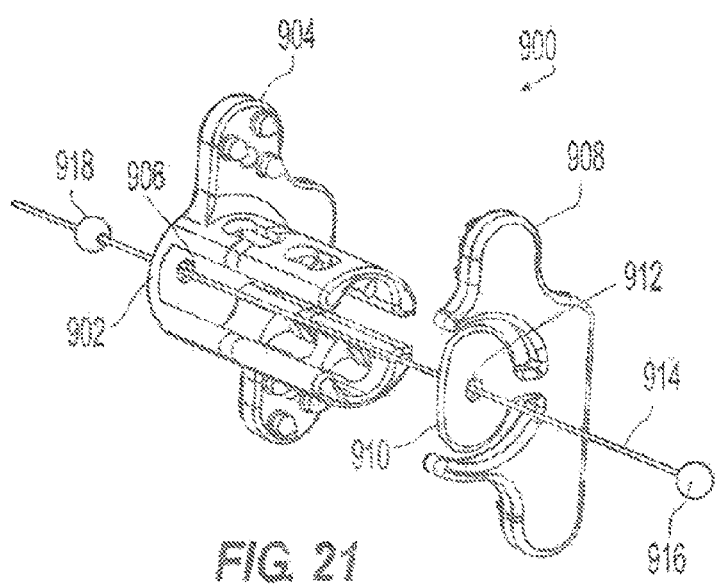

Referring to FIG. 21, an implant 900 is depicted that is configured generally like that of FIG. 16. However, an end wall 902 adjacent the first extension 904 includes a through bore 906 and the movable extension 908 includes a key 910 with a through bore 912. The bores 906, 912 receive a fastener to fix the extensions 904, 908 at a maximum spacing to prevent them from moving apart. Fasteners may include screws, bolts, nuts, cables, wires, ties, rods, and/or any other suitable fastener. In the example of FIG. 21, the fastener includes an elongated crimp receiving member 914, such as a cable, and crimp members 916, 918, such as ferrules or compressible beads.

Referring to FIG. 22, an implant 1000 includes a spacer 1002, a first extension 1004, and a second extension 1006. The spacer 1002 includes an outer surface 1008 defining one or more longitudinal grooves 1010 extending along the outer surface 1008 and through the first extension 1004. The first extension 1004 includes one or more corresponding slots 1012 having a radially outwardly extending portion 1014 through the first extension 1004 and communicating with the grooves 1010. The slots 1012 have a radially inwardly extending portion 1016 defining a shoulder 1018 at the end of the grooves 1010. The second extension 1006 includes one or more corresponding projections 1020 projecting longitudinally toward the first extension 1004 and terminating at a radially inwardly directed tab 1022. The second extension 1006 further includes a centering bore 1024 having a conical opening engageable with a conical free end 1026 of the spacer 1002. The second extension 1006 is attached to the spacer 1002 by pressing the tabs 1022 against the conical end 1026 of the spacer 1002 to deflect and spread the projections outwardly until the tabs 1022 engage the grooves 1010. The tabs 1022 are slid along the grooves 1010 until they exit through the slots 1012 and the tabs 1022 snap inwardly over the shoulders 1018 and into the portions 1016. Abutment of the tabs 1022 against the shoulders 1018 prevents the first and second extensions 1004, 1006 from moving apart. The engagement of the conical end 1026 of the spacer 1002 with the bore 1024 provides radial stability to the assembly.

Referring to FIG. 23, an implant 1100 includes a spacer 1102, a first extension 1104, and a second extension 1106. The spacer 1102 includes a transverse groove 1108 with a central boss 1110 having an enlarged head 1112. The second extension 1106 includes a portion 1114 sized to fit within the groove 1108 and an opening 1116 bordered by one or more angled tabs 1118. The second extension 1106 is assembled to the spacer by pressing the portion 1114 into the groove 1108 with the central boss 1110 directed into the opening 1116. As the central boss 1110 is pressed through the opening 1116, the tabs 1118 flex outwardly to allow central boss 1110 to pass. Once the central boss 1110 is past the tabs 1118, the tabs 1118 move to return to their original position and snap behind the enlarged head 1112. In this configuration, the central boss 1110 retains the second extension 1106 longitudinally and the groove 1108 prevents the second extension 1106 from rotating about the longitudinal axis of the implant 1100.

Referring to FIG. 24, an implant 1200 includes a spacer 1202, a first extension 1204, and a second extension 1206. The spacer 1202 includes a solid cylindrical sidewall 1208 defining a hollow interior 1210. The extensions 1204, 1206 are similarly configured and each includes a projection 1212, 1214 sized to fit inside of the spacer 1202. The extensions 1204, 1206 may attach to the spacer by press-fitting, snap-fitting, screwing, and/or otherwise engaging the projections 1212, 1214 with the spacer 1202. Alternatively, or additionally, the extensions 1204, 1206 may attach to the spacer 1202 with any of the previously depicted attachment mechanisms such as with a setscrew as shown in FIG. 3 or an elongated fastener as shown in FIG. 21. In the example of FIG. 24, the extensions 1204, 1206 are slotted longitudinally to form flexible petals 1216 that press into the spacer 1202. The extensions 1204, 1206 include openings 1218 to allow tissue growth, permit attachment of cerclage members, and/or receive additional fasteners attached to the spinous processes.

The spacer 1202 of FIG. 24 could have openings as shown in some of the other examples. Likewise, the other examples could have a solid surface as shown in FIG. 24. Similarly the extensions of any of the examples may be solid, have openings, or be otherwise advantageously configured.

Implants according to the present invention may be implanted using a variety of surgical approaches and techniques. Surgical approaches may include superspinous ligament sacrificing posterior approaches, superspinous ligament preserving posterior approaches, lateral approaches, and/or other suitable approaches. Techniques may include leaving the tissues at the surgical site unmodified or modifying the tissues such as trimming, rasping, roughening, and/or otherwise modifying them. For example, in FIG. 1, a lateral approach is used and the inferior spinous process is cut on its superior surface 26 to enlarge the interspinous space to receive the implant 100. After the interspinous space is prepared, the spacer 102 is inserted into the interspinous space. If a first extension 126 is present it may be pressed inwardly to lie near or abut one or more spinous processes. If a second extension 128 is used, it is engaged with the spacer 102 and also optionally pressed inwardly. In FIG. 1, opposing extensions 126, 128 having inwardly directed bone fasteners have been used and pressed inwardly so that the fasteners 132 engage the spinous processes 20, 21. The engagement of the fasteners 132 with the inferior spinous process 21 is not shown in FIG. 1.

Referring to FIGS. 25A-29 a spinous process implant 1250 similar to that of FIG. 1 includes a spacer 1252 having a first end 1254, a second end 1256, and a longitudinal axis 1258 extending from the first end 1254 to the second end 1256 along the spacer length direction 1. The spacer has a generally curved sidewall 1259 with a length that is generally parallel to the implant longitudinal axis 1258. Generally curved sidewall 1259 is separated along at least a portion of its length by a superior slot 1264a1 and an inferior slot 1264a2 to define first sidewall 1261a and second sidewall 1261b. Sidewall 1259 includes superior and inferior outer surfaces 1260, 1262. Slots 1264a1, 1264a2 and transverse openings 1264b, 1264c, and 1264d (FIG. 27) communicate from the superior and inferior outer surfaces 1260, 1262 inwardly to facilitate tissue growth. In certain exemplary embodiments, opening 1264b is not provided on second anterior sidewall 1261b. The exemplary spacer 1252 includes a hollow interior 1266 bounded by an inner surface 1268 such that the slots 1264a1, 1264a2, and openings 1264b, 1264c, and 1264d communicate from the outer surfaces 1260, 1262 to the hollow interior 1266.

The spinous process implant 1250 further includes a first extension 1270 projecting outwardly from the spacer 1252 transverse to the longitudinal axis 1258 to lie generally alongside either one or both of the superior and inferior spinous processes. In the exemplary embodiment of FIGS. 25A-29, the first extension 1270 extends both superiorly and inferiorly from spacer 1252 in the spacer height direction h. First extension 1270 defines a generally superior/inferior dimension 1272 (FIG. 27) along spacer height h which is greater than a generally superior/inferior dimension 1274 of the spacer 1252 (FIG. 27) along the spacer height direction h. Abutment of the first extension 1270 with the superior and inferior spinous processes helps to restrain spacer 1252 from moving laterally and to maintain the spacer 1252 between the spinous processes. In the illustrative embodiment of FIGS. 25A-29, the first extension 1270 also extends slightly posteriorly from spacer 1252 to define a posterior projection dimension 1276 (FIG. 26) along the spacer width direction w. The spacer 1252 defines a generally anterior/posterior dimension 1278 (FIG. 26) along the spacer width direction w and transverse to the spacer superior/inferior dimension 1274 (FIG. 27). When implant 1250 is implanted between the spinous processes of a patient, anterior sidewall 1261b is the anterior-most surface of implant 1250 while extension surface 1255 (FIGS. 25A and 25C) is the posterior-most surface of implant 1250.

In the exemplary embodiment of FIGS. 25A-D to 29, the anterior/posterior dimension 1278 is smaller than the superior/inferior dimension 1274, and the smaller anterior/posterior dimension 1278 is formed by relieving a portion 1280 of the anterior sidewall 1261b of the spacer 1252. In the exemplary embodiment, the longitudinal length (i.e., the length along the spacer length direction 1) of the spacer anterior sidewall 1261b is shorter than the longitudinal length of the spacer posterior sidewall 1261a by a distance 1282 equal to approximately one-fourth of the overall longitudinal length 1294 of the spinous process implant 1250. The exemplary spinous process implant 1250 includes a second extension (not shown but similar to those of the embodiments of FIGS. 1-24) mountable to the spacer 1252 for movement relative to the first extension 1270.

Figure 25A:
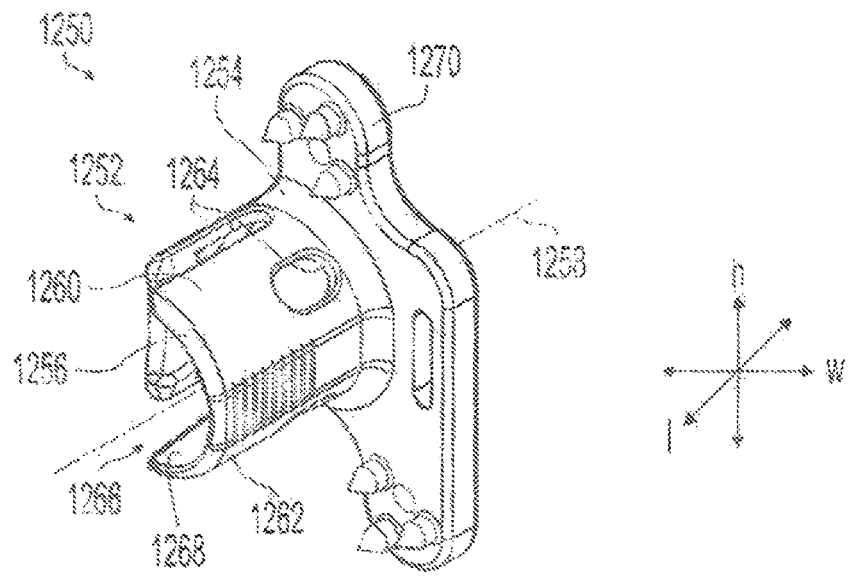
FIG. 25A is a perspective view of a modified version of the spinous process implant of FIG. 1.
Figure 25B:
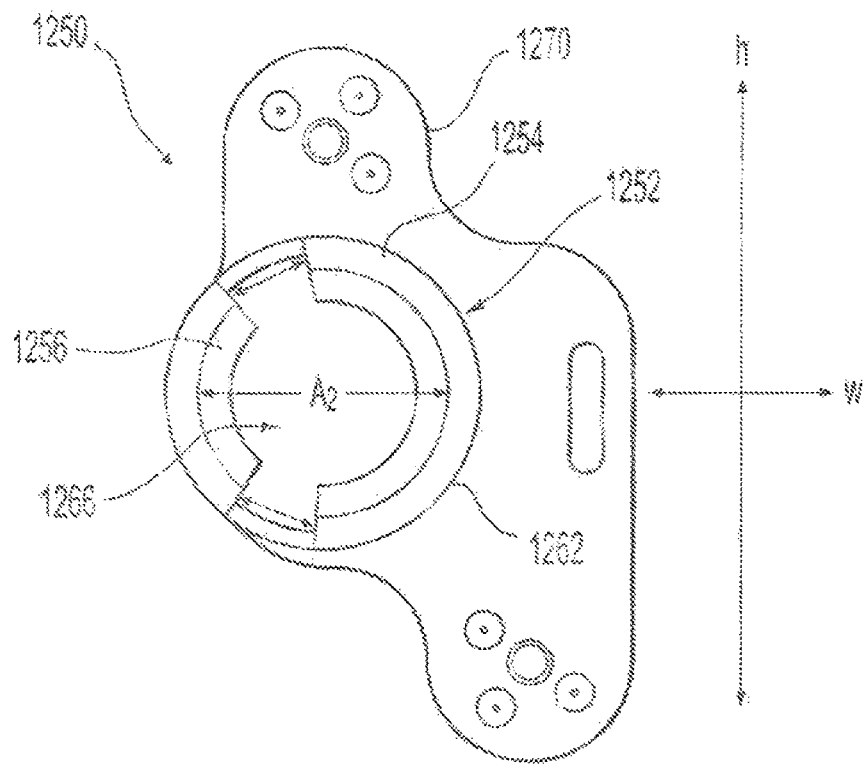
FIG. 25B is a first end elevational view of the spinous process implant of FIG. 25A.

Referring to FIG. 25B, an end view of spinous process implant 1250 as seen from spacer second end 1256 is provided. As depicted in the figure, anterior surface 1263 of spacer anterior sidewall 1261b includes a superior-most point 1269a and an inferior-most point 1269b. Correspondingly, posterior side wall surface 1265 of spacer posterior side wall 1261a includes superior-most point 1267a and inferior-most point 1267b. Note that "superior-most" and "interior-most" are for designation and do not necessarily coincide with the absolute superior and inferior point of the spacer 1252. The surface length of anterior surface 1263 of anterior sidewall 1261b as the anterior surface 1263 is traversed from superior-most point 1269a to inferior-most point 1269b (at a fixed position along the length of spacer 1252) is less than the surface length of posterior surface 1265 as the surface 1265 is traversed from superior-most point 1267a to inferior-most point 1267b (at a fixed position along the length of spacer 1252).

Figure 26:
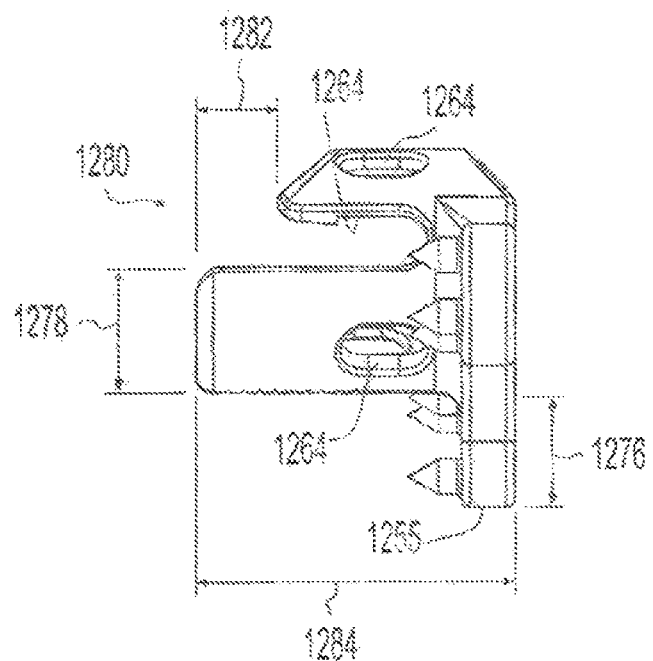
FIG. 26 is a top plan view of the spinous process implant of FIG. 25A.
Figure 27:
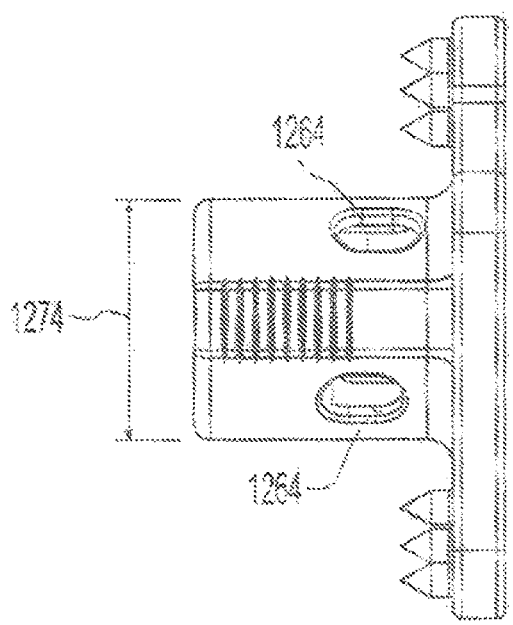
FIG. 27 is a posterior elevational view of the spinous process implant of FIG. 25A.

As shown in FIGS. 25B and 26, spacer anterior sidewall 1261b is spaced apart from spacer posterior sidewall 1261a along at least a portion of the length of spacer 1252 by a superior spacing distance $1_1$ and an inferior spacing distance $1_2$. Distances $1_1$ and $1_2$ correspond to the width of slots $1264_{a1}$ and $1264_{a2}$, and are typically, but not necessarily, equal. In addition, posterior side sidewall 1261a includes a partial, frusto-conical inner surface 1273 that slopes toward the interior 1266 and toward anterior sidewall 1261b of spacer 1252 as the frusto-conical inner surface 1273 is traversed along the spacer length direction 1 from the spacer second 1256 toward the spacer first end 1254.

Figure 25C:
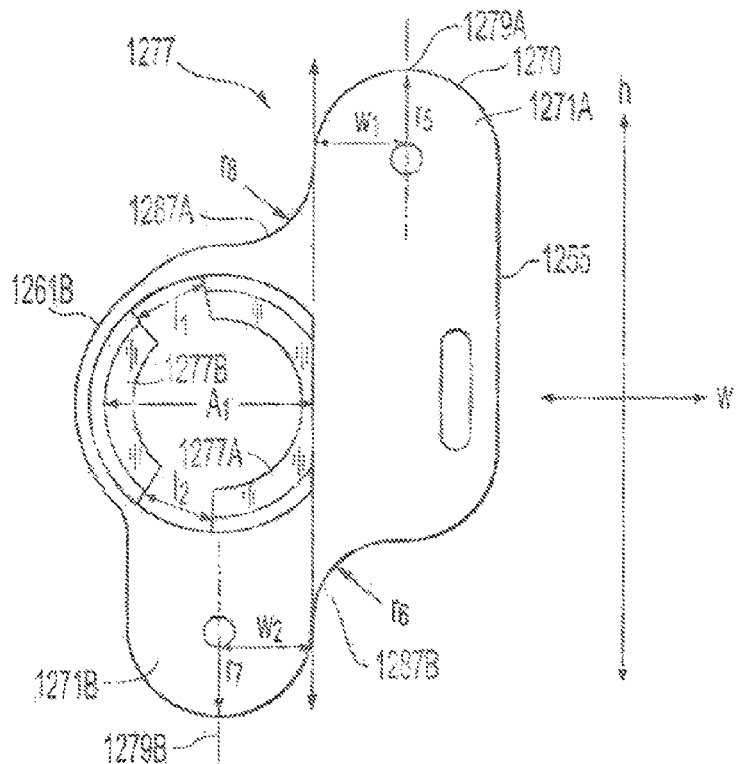
FIG. 25C is a second end elevational view of the spinous process implant of FIG. 25A.
Figure 25D:
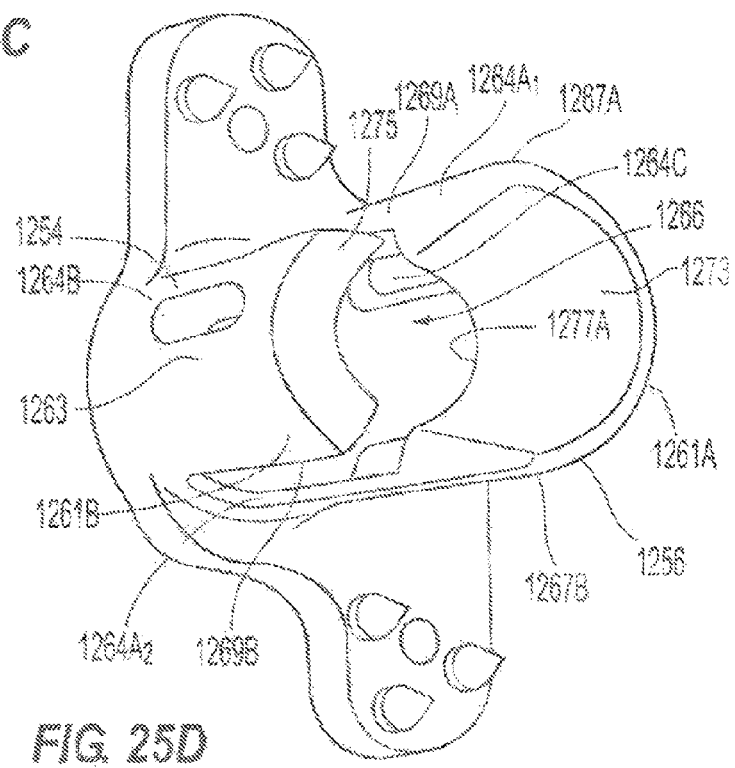
FIG. 25D is a perspective view of the spinous process implant of FIG. 25A.

In certain implementations, it may be advantageous to include bone growth promoting substance in the hollow interior 1266 of spacer 1252. To facilitate the insertion and retention of such material, spacer 1252 includes inwardly projecting posterior and anterior lips 1277a and 1277b (FIG. 25C). Inwardly projecting posterior lip 1277a is formed at the end of frusto-conical inner surface 1273 which is spaced apart longitudinally from spacer end 1256. Inwardly projecting anterior lip 1277b is formed proximate the free end of anterior sidewall 1261b. The inwardly projecting lips reduce the spacer's open cross-sectional area $A_2$ (FIG. 25B) at the free end of anterior sidewall 1261b (i.e., the end that is spaced apart from first extension 1270) relative to the spacer's open cross-sectional area $A_1$ at the spacer end proximate first extension 1270 (FIG. 25C). Thus, a bone growth promoting substance can be inserted into hollow interior 1266 at spacer first end 1254 and at least partially retained within hollow interior 1266 by lips 1277a and 1277b.

The spinous process implant 1250 may have a body configuration generally like any of the embodiments shown in FIGS. 1-24 and other suitable configurations. Preferably, at least the spacer second end 1256 has an anterior/posterior dimension 1278 (FIG. 26) along the spacer width direction w which is smaller than the superior/inferior dimension 1274 (FIG. 27) along the spacer height direction h. This relationship between dimensions 1274 and 1278 facilitates implantation, as described further below. Likewise, the spinous process implant 1250 may be used with a second extension generally configured like any of those illustrated in FIGS. 1-24 and other suitable configurations. Thus, in one example, the second extension includes tabs such as tabs 156 of second extension 128 (FIG. 3) which are engagable with spacer superior and inferior slots $1264a_1$ and $1264a_2$ to allow the second extension to slidably engage spacer 1252 along the spacer length direction 1 to adjust the distance between the first and second extensions along the spacer length direction 1. In addition, when the second extension is attached to spacer 1252, the first and second extensions provide a pair of superior lobes that are spaced apart long the spacer length direction 1 and a pair of inferior lobes that are spaced apart along the spacer length direction 1. In certain examples, the superior lobes of the first and second extensions are substantially aligned with one another when viewed along the spacer length direction 1, as indicated in the embodiment of FIGS. 4-6, as are the inferior lobes of the first and second extensions.

First extension 1270 has a geometry similar to that of extension 128 of FIG. 8. Referring to FIG. 25C first extension 1270 includes a first superior lobe 1271a and a second inferior lobe 1271b. First superior lobe 1271a and second inferior lobe 1271b are substantially co-planar to one another and are spaced apart from one another along the spacer height direction h. In addition, first superior lobe 1271a projects superiorly away from spacer 1252 while second inferior lobe 1271b projects inferiorly away from spacer 1252. In the embodiment of FIGS. 25A-25D, lobes 1271a and 1271b are integrally formed with spacer 1252 to define a unitary extension 1270. However, a multi-piece implant system may also be provided in which lobes 1271a and 1271b are not connected to spacer 1252 or to one another. While the lobes 1271a and 1271b are shown rounded, they may be squared, triangular, or other shaped.

As shown in FIG. 25C, first extension 1270 has a centerline 1277 defined along the spacer height direction h. First superior lobe 1271a has a centerline 1279a that is spaced apart posteriorly from first extension centerline 1277 by a distance $w_1$ while second inferior lobe 1271b has a centerline 1279b that is spaced apart anteriorly from first extension centerline 1277 by a distance $w_2$. In certain implementations, the distances between the lobe centerlines 1279a and 1279b and the first extension centerline 1277 are substantially equal.

Referring again to FIG. 25C, first superior lobe 1271a is posteriorly adjacent to first concave surface 1287a, while second inferior lobe 1271b is anteriorly adjacent to second concave surface 1287b. Multiple implants 1250 may be implanted between adjacent levels of the spine in the same manner as implant 100 shown in FIG. 9. First superior lobe 1271a is shaped to be complementary to second inferior concave surface 1287b such that when two spinal implants are placed on adjacent spinal levels, the first superior lobe 1271a of the inferior-most implant is interfittable into the second concave surface 1287b of the superior-most implant. Thus, first superior lobe 1271a has a radius of curvature $r_5$ that is substantially equal to the radius of curvature $r_6$ of the second concave surface 1287b. Similarly, the second inferior lobe 1271b is shaped to be complementary to the first superior concave surface 1287a such that when two spinal implants are placed on adjacent spinal levels, the second inferior lobe 1271b of the superior-most implant is interfittable with the first superior concave surface 1287a of the inferior-most implant. Thus, second inferior lobe 1271b has a radius of curvature $r_7$ that is substantially equal to the radius of curvature $r_8$ of the first concave surface.

Figure 28:
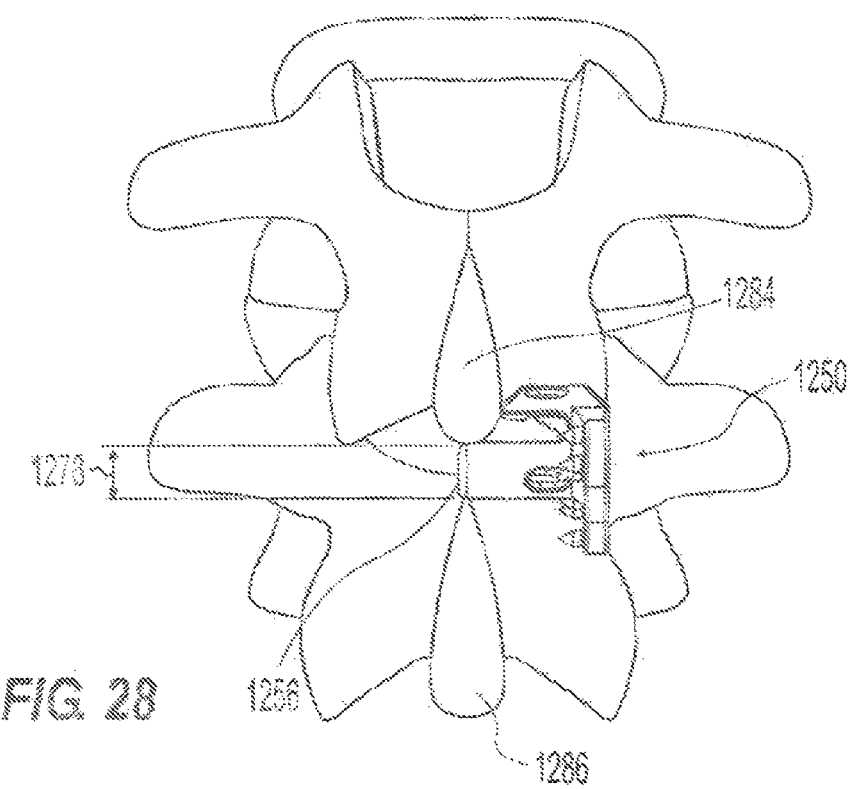
FIG. 28 is a posterior view of the spine showing insertion of the implant of FIG. 25A in a first inserted position between adjacent spinous processes.
Figure 29:
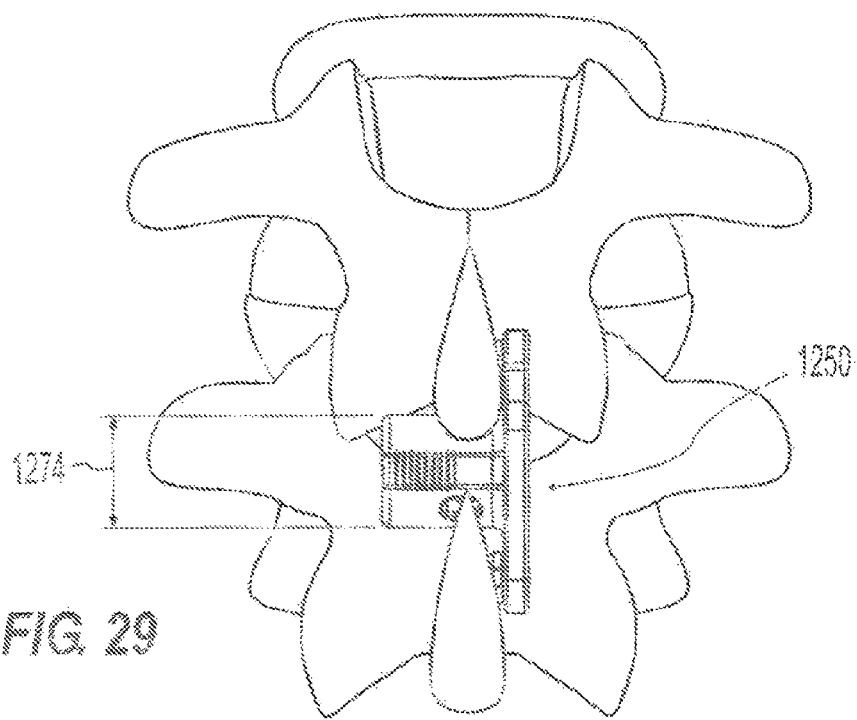
FIG. 29 is a posterior view of the spine showing insertion of the implant of FIG. 25A in a second inserted position between adjacent spinous processes.
Figure 32:
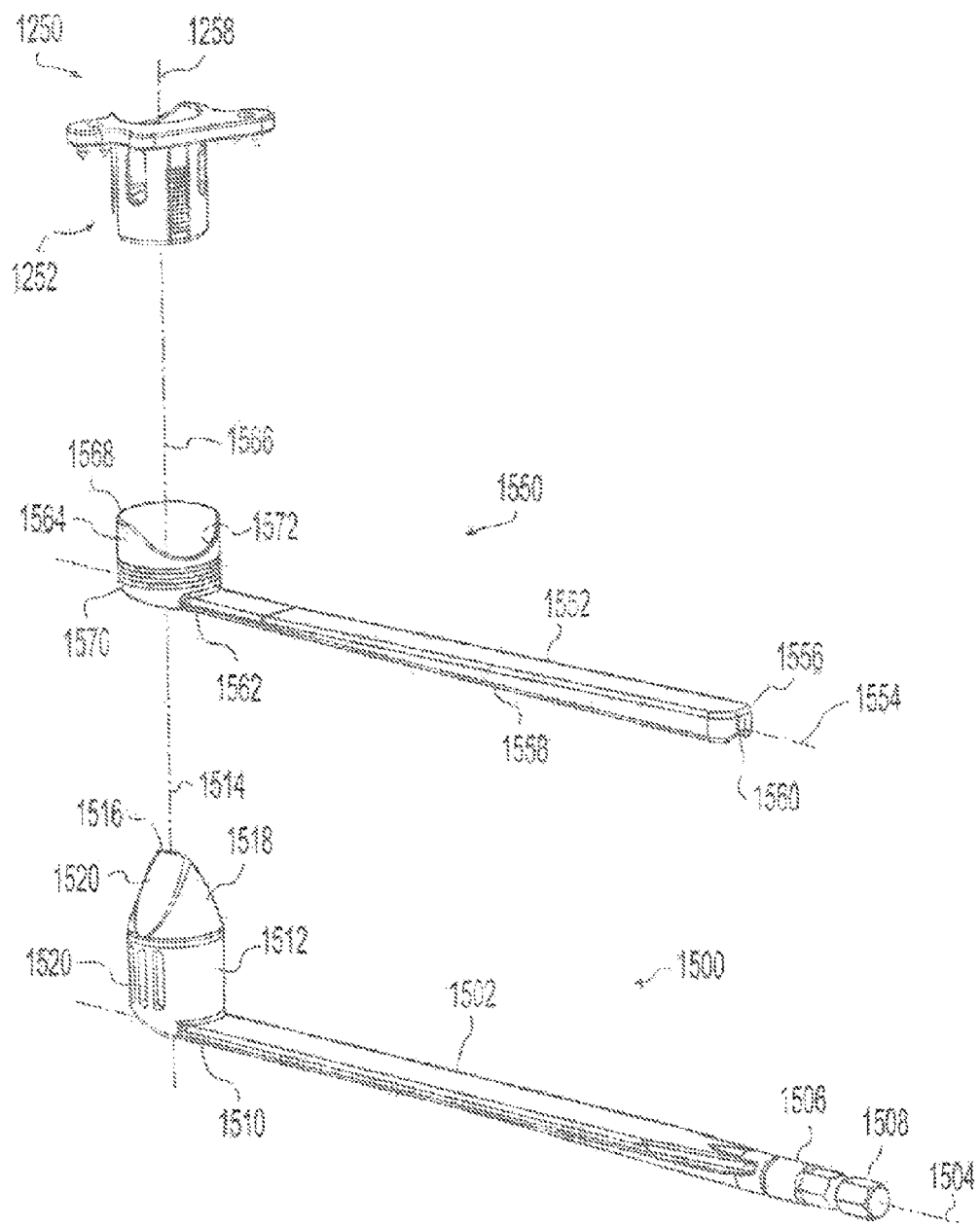
FIG. 32 is an exploded perspective view of a sleeve instrument and a trocar instrument useful for inserting implants like those of FIGS. 1-29, shown with the implant of FIG. 25A.

In use, the spinous process implant 1250 is initially implanted with the smaller anterior/posterior dimension 1278 of the spacer second end 1256 parallel to the superior/inferior spacing between adjacent spinous processes 1284, 1286 as shown in FIG. 28. In this orientation, the spinous process implant 1250 may be more easily inserted between the spinous processes 1284, 1286 (FIG. 28). Once the second end 1256 is inserted between the spinous processes 1284, 1286, the implant may be rotated to orient the larger superior/inferior dimension 1274 parallel to the superior/inferior spacing defined between the spinous processes 1284, 1286. The spinous process implant may then be moved into the fully inserted position of FIG. 29. A second extension, cerclage element, and/or other additional elements may then be implanted as desired and as described above relative to FIGS. 1-24.

An exemplary method of using the spinous process implant 1250 to treat a spinal disease of the type mentioned previously will now be described. In accordance with the method, two adjacent spinous processes are first selected based on an assessment of a spinal disease. The interspinous ligament between the selected spinous processes is either punctured or cut to allow implant 1250 to be positioned through the patient's sagittal plane. If desired, a bone growth promoting substance may be placed in hollow interior space 1266 of spacer 1252. As illustrated in FIG. 28, implant 1250 is inserted between the selected spinous processes with anterior/posterior dimension 1278 positioned in parallel to the superior-inferior spacing defined between the selected spinous processes. Once the implant 1250 is positioned between the selected spinous processes, the implant 1250 is rotated about the longitudinal axis 1258 of spacer 1252 until superior/inferior dimension 1274 is positioned in parallel to the superior-inferior spacing between the spinous processes. The first extension 1270 is then placed into abutting engagement with the selected spinous processes. At this point, spacer second end 1256 projects through and beyond the patient's sagittal plane. If fasteners are provided on first extension 1270, they may be engaged with the superior and inferior spinous processes on one side of the patient's sagittal plane.

If desired, a second extension such as second extension 128 of FIGS. 3-8 may then be movably attached to spacer 1252 by slidably engaging tabs 156 with superior and inferior spacer slots 1264$a_1$ and 1264$a_2$. The second extension 128 is then medially slid along the spacer length 1 toward the patient's sagittal plane until second extension 128 comes into abutting engagement with the selected spinous processes. Once the desired position is reached, set screw 130 may be used to fix the position of second extension 128 along the spacer length 1.

Referring to FIGS. 30 and 31, introducers in the form of a set of instruments 1300 are provided to facilitate lateral insertion of an implant into the interspinous space. The set of instruments includes a plurality of inserters 1302, 1303 in which each inserter 1302, 1303 has a first or handle portion 1304 and a second or working portion 1306. The working portion 1306 is insertable into the interspinous space. Preferably, the handle portion 1304 extends transversely to the working portion 1306 to facilitate holding and manipulating the inserter 1302, 1303 while the working portion 1306 is in the interspinous space. The handle portion 1304 and working portion 1306 may define a curve, angle, offset, and/or any other suitable transverse orientation. In the example of FIG. 30, the inserters 1302, 1303 are generally "L"-shaped. The working portion 1306 tapers from a relatively larger cross-sectional dimension at a first portion 1307 spaced away from its free end 1308 to a relatively smaller cross-sectional dimension at its free end 1308. In the illustrative embodiment, the working portion is conical and tapers from a larger diameter to a smaller diameter. The free end 1308 of inserter 1303 defines a hollow tip having an opening 1310. The set of instruments 1300 is provided with a plurality of similarly configured inserters having differently sized working portions 1306 such that the free end 1308 of one inserter 1302 will fit inside the opening 1310 at the tip of another inserter 1303. Optionally, the working portion 1306 may be separated into opposing halves attached to opposing handles 1314, 1316. As the opposing handles 1314, 1316 are moved relative to one another, the opposing halves of the working portion 1306 move relative to one another. In the illustrative embodiment, squeezing the handles 1314, 1316 toward one another causes the working portion 1306 to expand as the opposing halves of the working portion 1306 open outwardly away from one another.

In use, a first inserter 1302 is inserted into the interspinous space. The first inserter 1302 is relatively small to ease insertion. As the free end 1308 is inserted further, the tapered working portion 1306 expands the interspinous space. Optionally, the interspinous space can be further expanded by expanding the working portion while it is inside the interspinous space such as by squeezing the handles 1314, 1316. A second, larger inserter 1303 is engaged with the first inserter 1302 by placing its hollow tip over the tip of the first inserter 1302 and then passing the overlapping instruments back through the interspinous space to remove the first inserter 1302 and insert the second inserter 1303. As the end of the second inserter 1303 is inserted further, the tapered working portion expands the interspinous space. Optionally, the interspinous space can be further expanded by expanding the working portion 1306 while it is inside the interspinous space. Progressively larger inserters can be inserted in this fashion until the interspinous space has been expanded to the desired size. Once the desired size has been reached the appropriate implant size may be determined by noting the size of the last inserter. The inserter may optionally include indicia 1320 on the tapered working portion 1306 corresponding to different spacer sizes to further facilitate sizing the implant. The implant is inserted by engaging the spacer 1402 (FIG. 31) with the working portion 1306 of the second inserter 1303 as shown in FIG. 31. The implant may be engaged inside of the hollow tip of the inserter or the tip of the inserter may engage a hollow tip on the implant as shown. The spacer 1402 is pulled into the interspinous space as second inserter 1303 is withdrawn. If desired, a second extension may then be attached to the spacer body as described earlier with respect to FIGS. 1-24.

Referring to FIGS. 32-37, introducers in the form of a trocar instrument 1500 and a sleeve instrument 1550, are shown with the spinous process implant 1250 of FIG. 25. The trocar instrument 1500 includes a handle 1502 extending generally parallel to a handle axis 1504. In the illustrative embodiment, the handle 1502 is generally round at a proximal end 1506 and is generally thinner and more rectangular distally. The proximal end 1506 includes an attachment portion 1508 for connecting to another instrument, grip, or the like. The distal end 1510 of the handle 1502 connects to a head 1512 that extends outwardly from the handle 1502 generally transverse to the handle axis 1504 and generally parallel to a head axis 1514. The head 1512 may be cylindrical, egg shaped, polygonal, and/or any other shape. In the illustrative embodiment of FIG. 32, the head is generally cylindrical about the head axis 1514. A tapered leading end 1516 projects from the head generally along the head axis 1514 to ease insertion of the head 1512 between adjacent spinous processes. The leading end 1516 may be conical, prismatic, and/or any other suitable shape. In the illustrative embodiment of FIG. 32, the leading end 1516 is a blend of a cylinder and a prism defined by opposing, cylindrical sides 1518 (one of which is shown) that are generally mirror images of one another and converging planar sides 1520 (one of which is shown) that are adjacent to and disposed between the opposing cylindrical sides 1518. This configuration allows the planar sides 1520 to be inserted between adjacent spinous processes and the head 1512 to be rotated about the head axis 1514 to pry the spinous processes apart. With partial insertion of the leading end 1516, the head 1512 may be rotated to open the interspinous space to permit further insertion until the head 1512 can be fully inserted between the spinous processes. The head 1512 further includes a rasp portion 1522 on the sides of the head 1512. In the illustrative embodiment, the rasp portion 1522 includes a plurality of cutters formed on opposite sides of the head 1512. The illustrative cutters are depressions having sharp edges at the head surface. With the head 1512 fully inserted between the spinous processes, the spinous processes will press into the rasp portion 1522 depressions such that rotation of the head 1512 about the head axis 1514 will rasp away soft tissues, the bone surface, and/or other tissues to prepare the spinous processes for receiving the spinous process implant 1250. By preparing the spinous processes, the growth of bone between the spinous processes, into, onto, and/or through the spinous process implant 1250 is enhanced.

Figure 33:
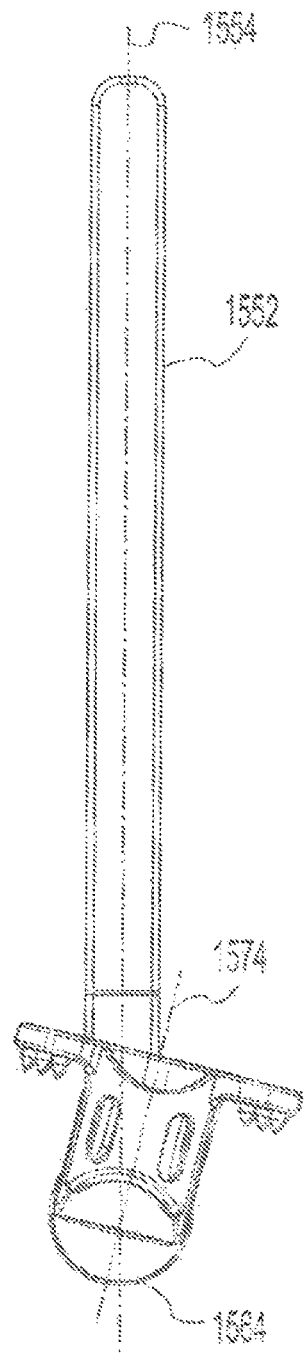
FIG. 33 is a side elevation view of the sleeve instrument of FIG. 32 shown with the implant of FIG. 25A installed thereon.

The sleeve instrument 1550 includes a handle 1552 extending generally parallel to a handle axis 1554. In the illustrative embodiment, the handle 1552 is generally rectangular at a proximal end 1556 and becomes thinner distally. The back 1558 of the handle 1552 is generally flat and includes a concave portion 1560 on the back of the handle at the proximal end 1556. The handle distal end 1562 connects to a sleeve 1564 that extends outwardly from the handle 1552 generally transversely to the handle axis 1554 and generally parallel to a sleeve axis 1566 to a leading end defined by a rim 1568. The sleeve 1564 may be cylindrical, elliptical, polygonal, and/or any other suitable shape. In the illustrative embodiment of FIG. 32, the sleeve 1564 is generally cylindrical and is sized to slide over the trocar instrument head 1512 in close fitting relationship. With the sleeve 1564 slid over the trocar instrument head 1512, the flat back 1558 of the sleeve instrument handle 1552 lies flat against the flat front surface of the trocar instrument handle 1502 and the rounded portion of the proximal end 1506 of the trocar instrument handle 1502 nests in the concave portion 1560 of sleeve instrument handle 1552. With both handles 1502, 1552 being relatively thin near the distal ends 1510, 1562, the handles 1507, 1552 occupy less space distally and fit more easily into a surgical site while maximizing the extension of the sleeve 1564 and head 1512 from the handles 1502, 1552. The sleeve 1564 further includes a series of annular grooves 1570, or alternatively ridges, that enhance the engagement of the spinous processes with the outer surface of the sleeve 1564 to resist slipping of the sleeve from between the spinous processes. The sleeve 1564 further includes a relieved portion 1572 defining a first region of rim 1568 that is spaced apart from handle 1552 by a distance that is less than the distance by which rim 1568 is spaced apart from handle 1552 in a second region located away from relieved portion 1572. The sleeve 1564 is sized to engage the spinous process implant 1250. In the illustrative embodiment of FIG. 32 the sleeve 1564 is sized with an internal dimension able to receive the spacer 1252 in close-fit sliding relationship along the sleeve axis 1566. Also in the illustrative embodiment, the relieved portion 1572 is sized to receive the spacer transverse to the sleeve axis 1566 in sliding relationship along the relieved portion 1572 to ease insertion of the spacer into the sleeve 1564 as will be discussed more fully below. In the illustrative embodiment, the relieved portion mid-point 1573 is positioned on the rim 1568 at a position offset from the handle axis 1554 so that the spinous process implant 1250 engages the relieved portion 1572 along an engagement axis 1574 angled relative to the handle axis 1554 as shown in FIG. 33. In the illustrative embodiment of FIG. 33, the angle between the engagement axis 1574 and the handle axis 1554 is in the range of 0 to about 90 degrees; more particularly 0 to about 40 degrees; more particularly about 20 degrees. By positioning the relieved portion mid-point 1573 at an angle relative to the handle axis 1554, the handle 1552 and a user's hand do not block the insertion path of the spinous process implant 1250. The trocar instrument 1500 and sleeve instrument 1550 may be provided in a plurality of sizes corresponding to a plurality of sizes of spinous process implants 1250.

Figure 34:
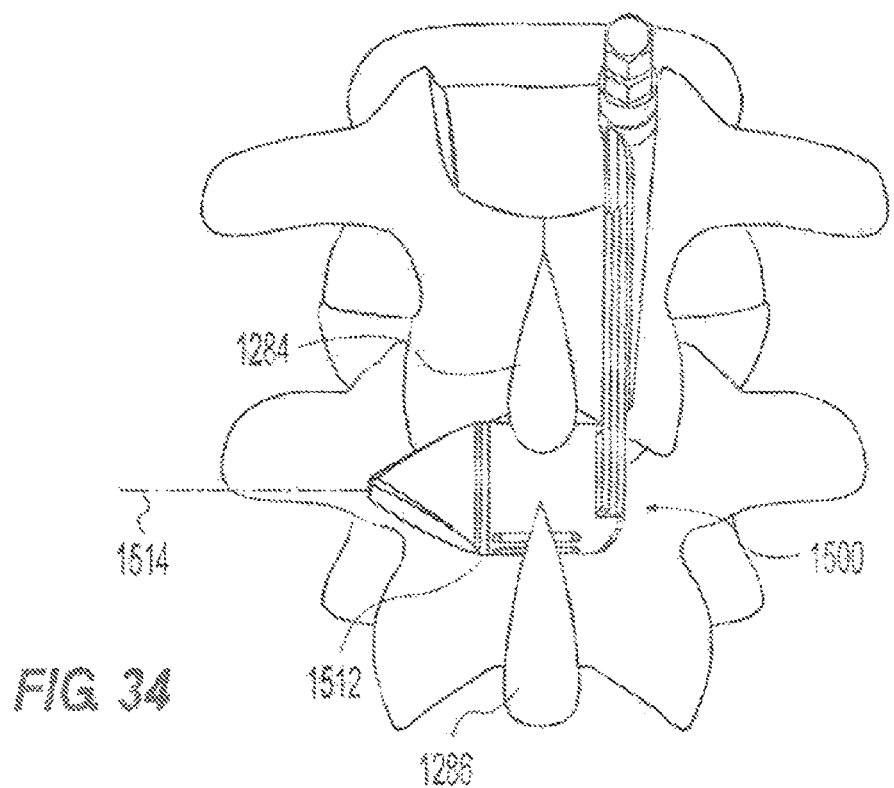
FIG. 34 is a posterior view of the spine showing the trocar of FIG. 32 in vivo in a first inserted position between adjacent spinous processes.
Figure 35:
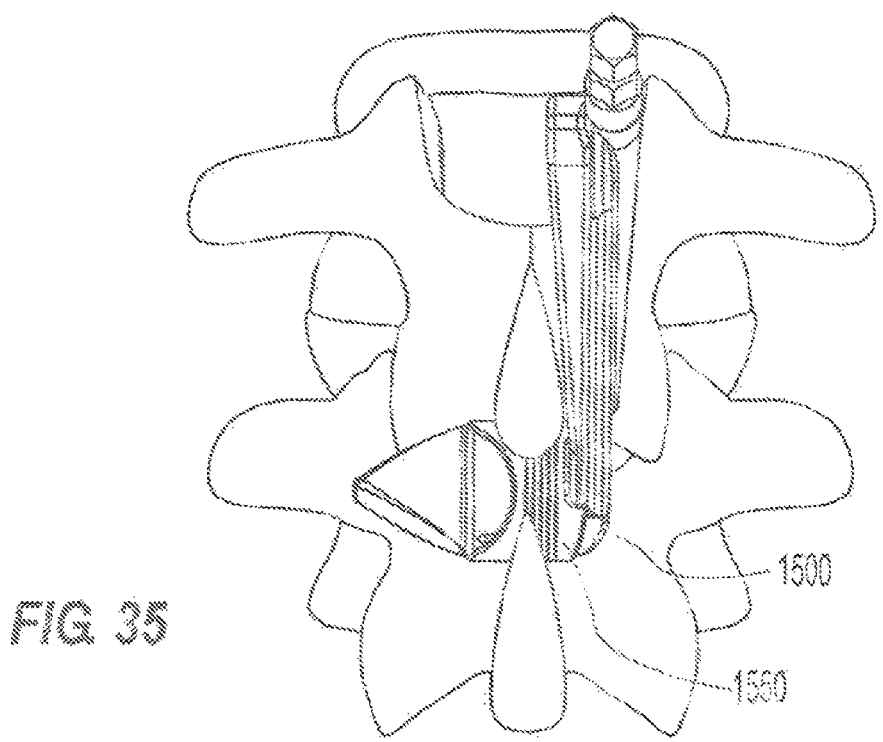
FIG. 35 is a posterior view of the spine showing the trocar and sleeve of FIG. 32 in vivo in a second inserted position between adjacent spinous processes.
Figure 36:
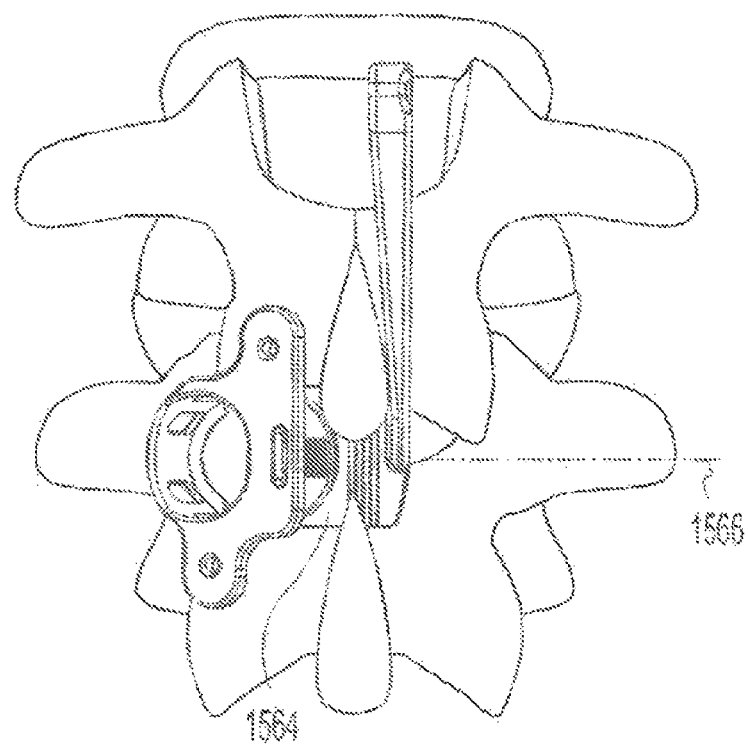
FIG. 36 is a posterior view of the spine showing the sleeve of FIG. 32 and the implant of FIG. 25A in vivo in a first inserted position between adjacent spinous processes.
Figure 37:
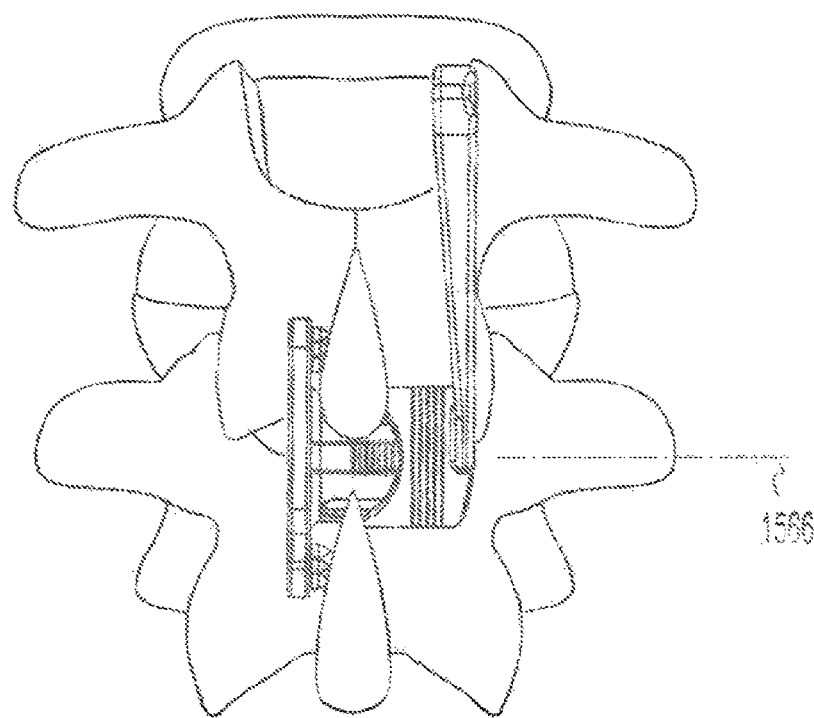
FIG. 37 is a posterior view of the spine showing the sleeve of FIG. 32 and the implant of FIG. 25A in vivo in a second inserted position between adjacent spinous processes.

FIGS. 34-37 illustrate the use of the trocar instrument 1500 and sleeve instrument 1550 in accordance with a method of implanting the spinous process implant 1250 between a patient's adjacent spinous processes. The interspinous ligament is first removed or penetrated such that the head 1512 extends into and through the patient's sagittal plane. In FIG. 34 the head 1512 of the trocar instrument 1500 has been worked between adjacent spinous processes 1284, 1286 and the head is rotated back and forth about the head axis 1514 to rasp the opposed surfaces of the adjacent spinous processes 1284, 1286 to prepare them for receiving the spinous process implant 1250. The trocar instrument 1500 is removed and engaged with sleeve instrument 1550 and the assembly is reinserted between the spinous processes as shown in FIG. 35. The trocar instrument 1500 is then removed leaving the sleeve instrument 1550 in place. Alternatively, the sleeve instrument 1550 may be inserted between the spinous processes after removal of the trocar instrument 1500 without engaging the trocar instrument 1500 with the sleeve instrument 1550. As shown in FIG. 36, the spinous process implant 1250 is inserted into the sleeve 1564 by engaging the spacer 1252 with the relieved portion 1572 along the engagement axis 1574 and then rotating the spinous process implant 1250 until its longitudinal axis 1258 is parallel to the sleeve axis 1566 while simultaneously pressing the spacer 1252 into the sleeve 1564. The spinous process implant 1250 is pressed into the sleeve 1564 until the spinous process implant is seated as shown in FIG. 37. The sleeve instrument 1550 is then removed and a second extension, cerclage element, and/or other additional elements may then be implanted as desired and as described above relative to FIGS. 1-24. By using the relieved portion 1572 as described above, the size of the incision needed to implant the spinous process implant 1250 may be minimized. Alternatively, the spinous process implant 1250 may be inserted along the sleeve axis 1566 without first engaging the relieved portion and rotating the spinous process implant 1250. Also, alternatively, the spinous process implant 1250 may be only partially inserted before the sleeve instrument 1550 is removed and the spinous process implant 1250 then subsequently seated.

Figure 38:
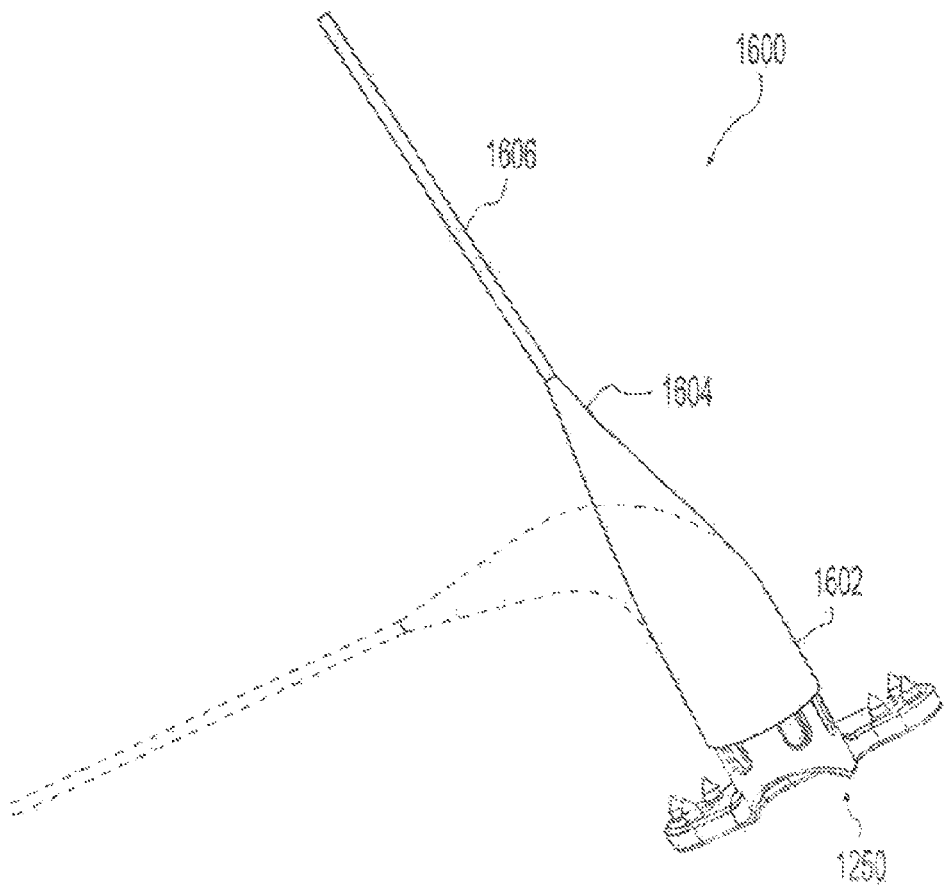
FIG. 38 is a perspective view of an instrument useful for inserting the implants of FIGS. 1-29 shown with the implant of FIG. 25.
Figure 39:
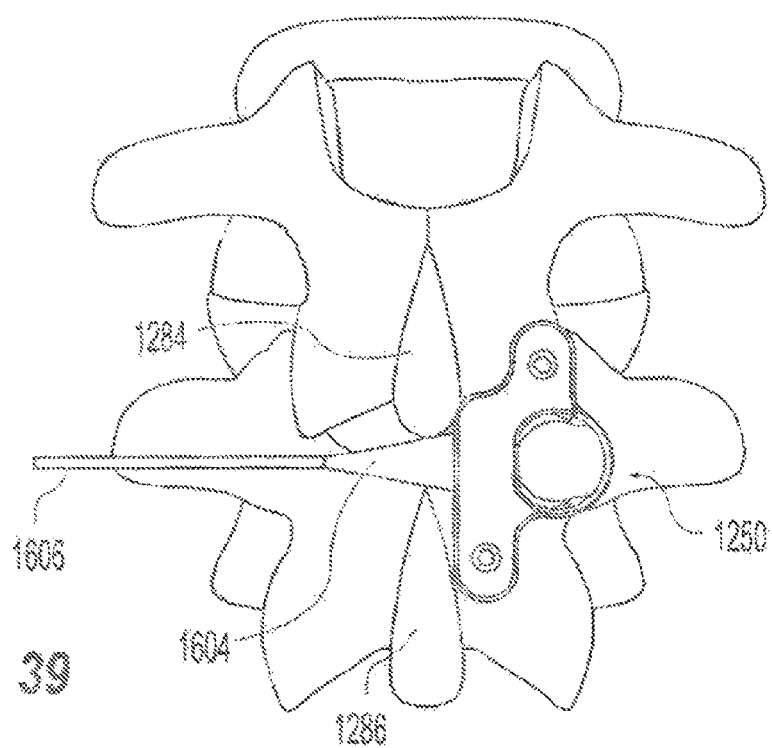
FIG. 39 is a posterior view of the spine showing the instrument of FIG. 38 and the implant of FIG. 25 in vivo in a first inserted position between adjacent spinous processes.
Figure 40:
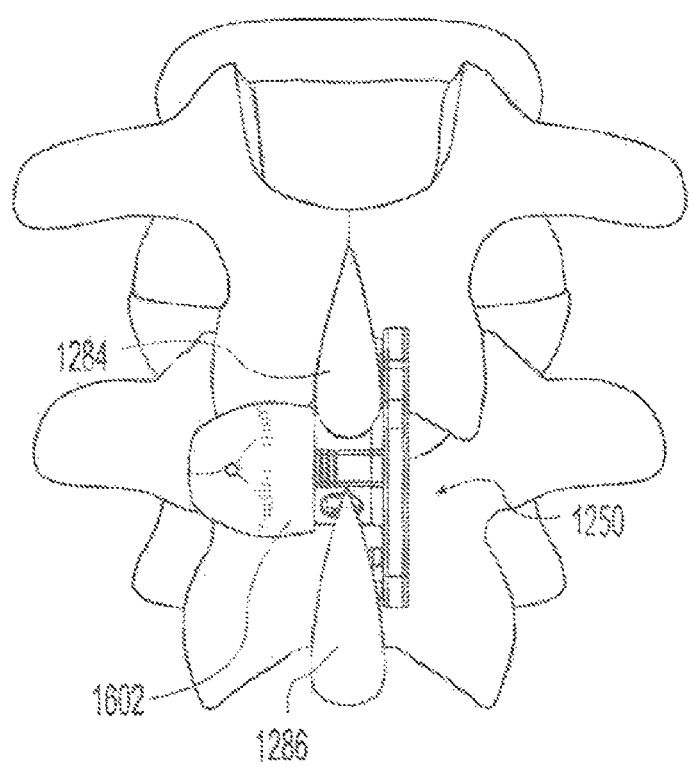
FIG. 40 is a posterior view of the spine showing the instrument of FIG. 38 and the implant of FIG. 25 in vivo in a second inserted position between adjacent spinous processes.
Figure 41:
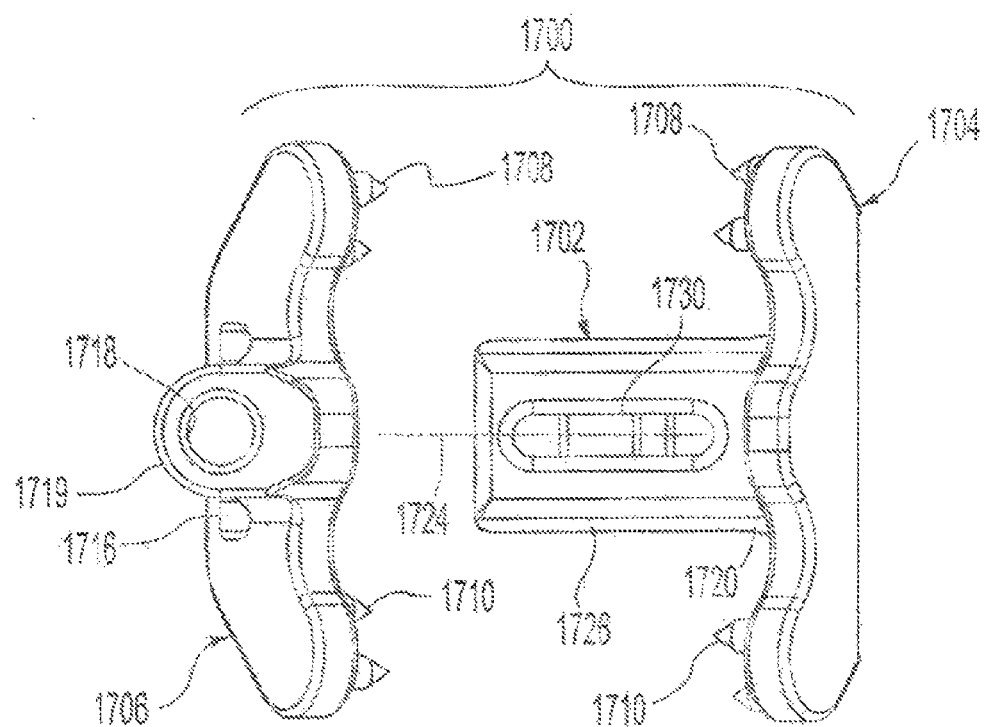
FIG. 41 is an exploded elevation view of a posterior side of an example of interspinous implant of the present invention.

Referring to FIGS. 38-40, an introducer in the form of a flexible guide 1600 includes an engaging portion 1602, a relatively narrow leader 1606, and a transition portion 1604 tapering between the engaging portion 1602 and the leader 1606. The guide 1600 includes a flexible material allowing all or part of the guide 1600 to bend to facilitate pulling the guide 1600 between adjacent spinous processes. In the illustrative embodiment of FIG. 38, the entire guide 1600 is formed of a flexible material such as polysiloxanes, natural rubber, synthetic rubber, polyethylene, polyester, polytetrafluoroethylene, and/or any other suitable material. The guide 1600 may be molded, cast, extruded, machined, braided, woven, wrapped, and/or otherwise formed. The engaging portion 1602, transition portion 1604, and leader 1606 may be made in one piece or made as discrete components and joined together. In the illustrative embodiment of FIG. 38, the guide 1600 is molded as one piece of synthetic rubber. The engaging portion 1602 may engage the spinous process implant 1250 positively and/or frictionally. The engaging portion 1602 may engage inside and/or outside of the spinous process implant 1250. In the illustrative embodiment of FIG. 38, the engaging portion comprises a hollow sleeve that stretches to frictionally grip the outer surface of the spacer 1252.

In use, the leader 1606 is passed between adjacent spinous processes 1284, 1286 and used to pull the transition portion 1604 between the spinous processes 1284, 1286 as shown in FIG. 39. The spinous process implant 1250 is pressed into place and rotated as the leader 1606 is pulled further to guide the spinous process implant 1250 between the spinous processes 1284, 1286 as shown in FIG. 40. The guide 1600 is then removed and a second extension, cerclage element, and/or other additional elements may then, be implanted as desired and as described above relative to FIGS. 1-24.

Referring now to FIGS. 41-44, another example of interspinous implant 1700 is shown and described. The interspinous implant 1700 includes a spacer 1702, a first extension or plate 1704, and a second extension or plate 1706. The spacer 1702 may be adjustably or permanently connected to either one or both of the first and second extensions 1704, 1706. In one example, the spacer 1702 is permanently connected to the first extension 1704 and the second extension 1706 may be adjustably connected to the spacer 1702 (e.g., axially moveable along a length of the spacer 1702 and fixed at an adjusted position).

The spacer 1702 may include first and second ends 1720, 1722 spaced apart along a longitudinal axis 1724. The spacer 1702 may further include first and second sidewall portions 1726, 1728 (FIGS. 41 and 44), at least one of the first and second sidewall portions 1726, 1728 may include one or more slot features 1730, which in this exemplary spacer 1702 has a slot 1730 in the posterior portion of the first sidewall portion 1726. The slot 1730 may allow implanting fusion material into the space and provides additional tissue in-growth paths among other things. The first and second sidewall portions 1726, 1728 may be divided by at least one slot feature 1732 in the superior and inferior surfaces of spacer 1702. The first and second sidewall portions 1726, 1728 may have different lengths, shapes and sizes.

Each of the first and second extensions 1704, 1706 may extend in superior and inferior directions relative to the spacer 1702. Each of the first and second extensions 1704, 1706 may include a first set of fasteners 1708, such as, spikes, pins, screws, nails, etc. and a second set of fasteners 1710, such as, spikes, pins, screws, nails, etc. that extend from a contact surface 1712 of first and second extensions 1704, 1706 (best seen in FIG. 43). The contact surfaces 1712 are arranged to face and contact one or more spinous processes as previously described herein. The first and second sets of fasteners 1708, 1710 are shown extending perpendicular from the contact surfaces 1712 and are intended to grip posterior elements of the spine such as, for example, the spinous processes, lamina, or combination thereof of a patient. The fasteners 1708, 1710 may be mounted at an angle other than perpendicular to the contact surfaces to fit a particular anatomy. As described with respect to FIG. 3, the fasteners 1708, 1710 may have some freedom to angelate with respect to contact surfaces 1712.

Figure 44:
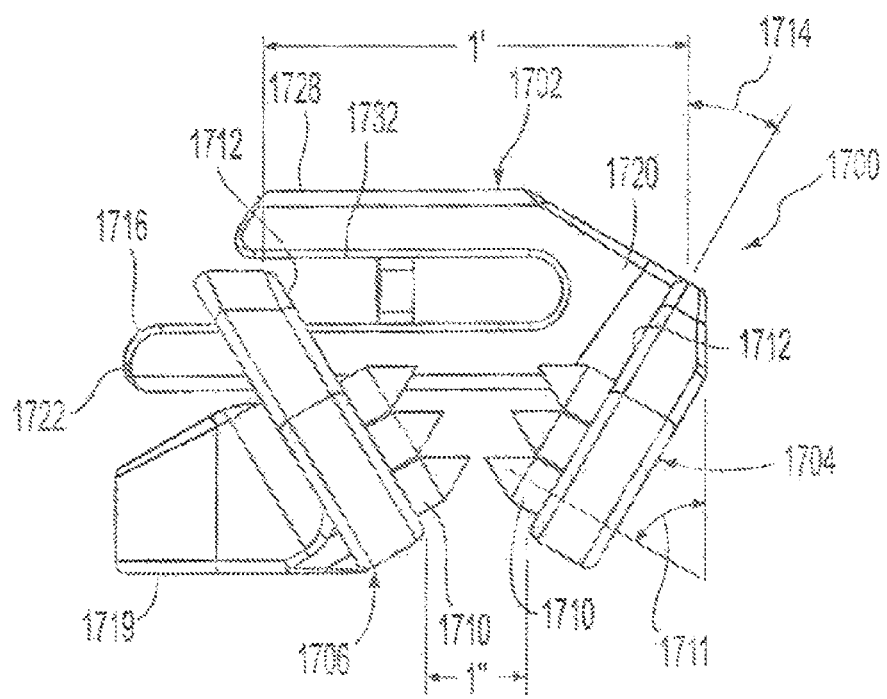
FIG. 44 is a top view of the interspinous implant of FIG. 41.
Figure 45:
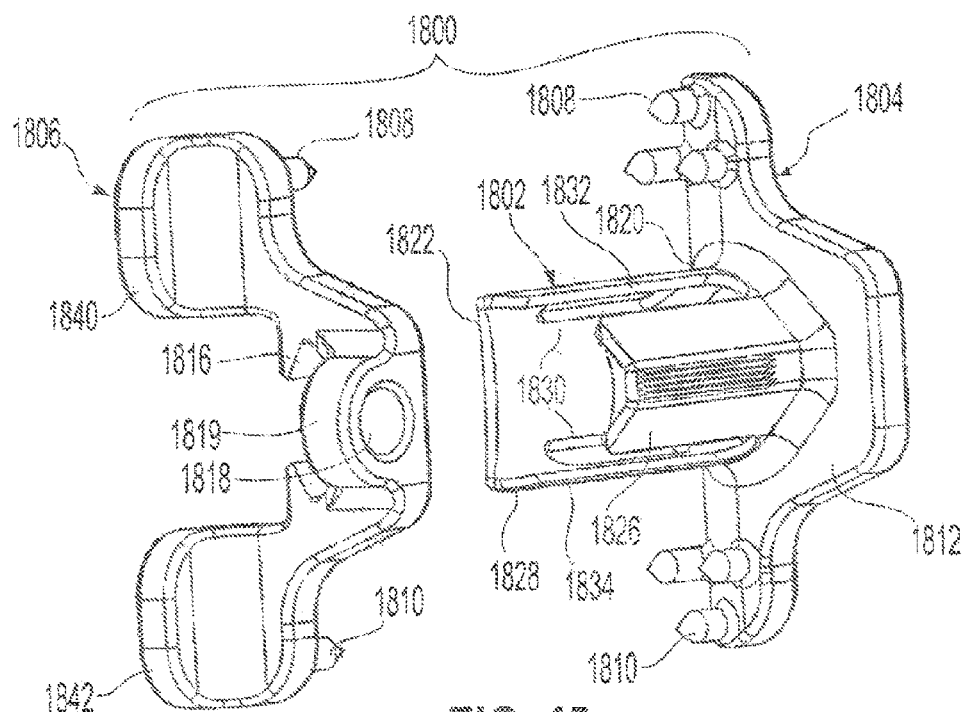
FIG. 45 is an exploded perspective view of another example interspinous implant of the present invention.
Figure 46:
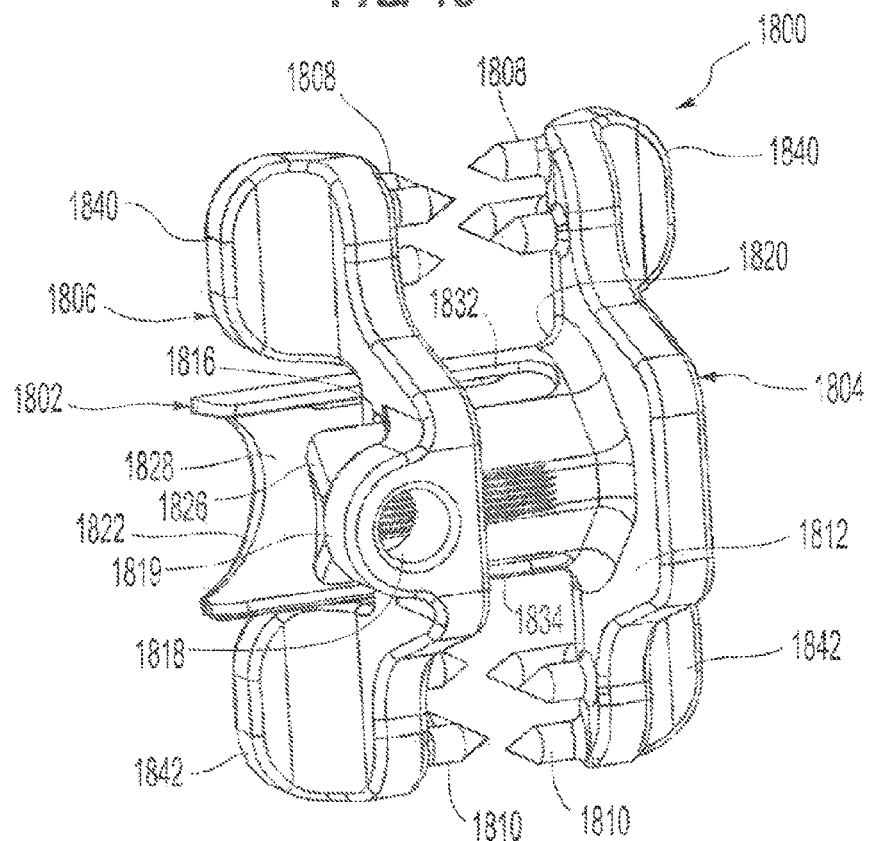
FIG. 46 is a perspective view of the interspinous implant of FIG. 45.
Figure 47:
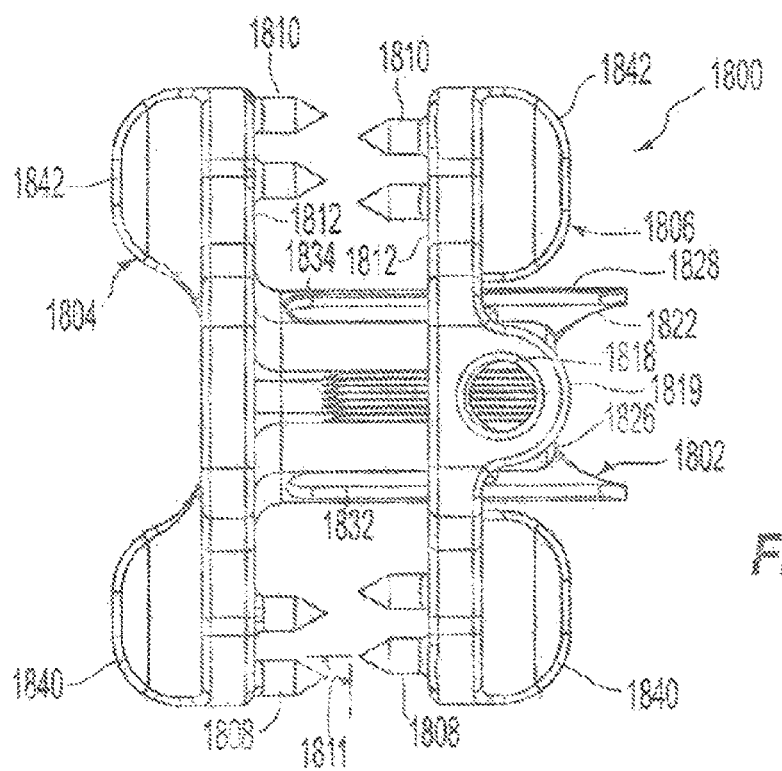
FIG. 47 is an elevation view of a posterior side of an interspinous implant of the present invention.

The contact surfaces 1712 are arranged at an acute angle 1714 relative to a line perpendicular to the longitudinal axis 1724 of the spacer 1702 when the interspinous implant 1700 is assembled as shown in FIG. 44. In one example, the angle 1714 is in the range of about 0° to about 45°, and more preferably in the range of about 20° to about 30°. The contact surfaces 1712 are angled anteriorly so that the first and second sets of fasteners 1708, 1710 are directed toward the sagittal plane and anteriorly. In other words, the contact surfaces 1712 converge in an anterior to posterior direction. The first and second sets of fasteners 1708, 1710 may be adapted to seat in an anterior portion of the spinous processes, a junction between the lamina and spinous processes, or in a portion of the lamina, to provide fixation in a bone of that portion of the spine, which may be relatively stronger bone. The angled arrangement of the first and second extensions 1704, 1706 relative to the spacer 1702 may be particularly well suited for connection to the L5-S1 vertebrae given the small or nonexistent spinous process often associated with S1. The angled arrangement of the first and second extensions 1704, 1706 may provide a first distance 1' at the anterior edge of the contact surface 1712, and a second distance 1" at the posterior edge of the contact surfaces 1712 (FIG. 44).

In alternative arrangements, the contact surfaces 1712 of the first and second extensions 1704, 1706 may be arranged at different angles relative to the longitudinal axis 1724 of the spacer 1702. For example, one of the contact surfaces 1712 may be arranged perpendicular to the longitudinal axis 1724 and the other of the contact surfaces 1712 may be arranged at an angle 1714 that is non-perpendicular to the longitudinal axis 1724.

An orientation of the first and second sets of fasteners, 1708, 1710 may be at an angle 1711 relative to the line that is perpendicular to the longitudinal axis 1724. In some cases, the angle 1711 may be perpendicular the contact surfaces 1712. However, angle 1711 may be other than 90° such that the sets of fasteners 1708, 1710 have more or less penetration into bone pursuant to patient needs. In some arrangements, the first and second sets of fasteners 1708, 1710 may be arranged parallel with each other regardless of the angle 1714 of the contact surfaces 1712.

In the example shown, the second extension 1706 is separate from spacer 1702 and translatable relative to spacer 1702 along longitudinal axis 1724. Thus, the second extension 1706 may include a mounting portion 1719 to releasably attach second extension 1706 to spacer 1702. The mounting portion 1719 defines a set screw bore 1718. A set screw, such as set screw 130 as shown in FIG. 3 may be threadably mated with the set screw bore 1718 and extend into contact with a portion of the spacer 1702 (e.g., the first sidewall portion 1726) to secure the second extension 1706 to the spacer 1702 in a fixed axial position, in particular, the sides of slot 1730 may be tapered to engage the tip of a set screw.

Figure 42:
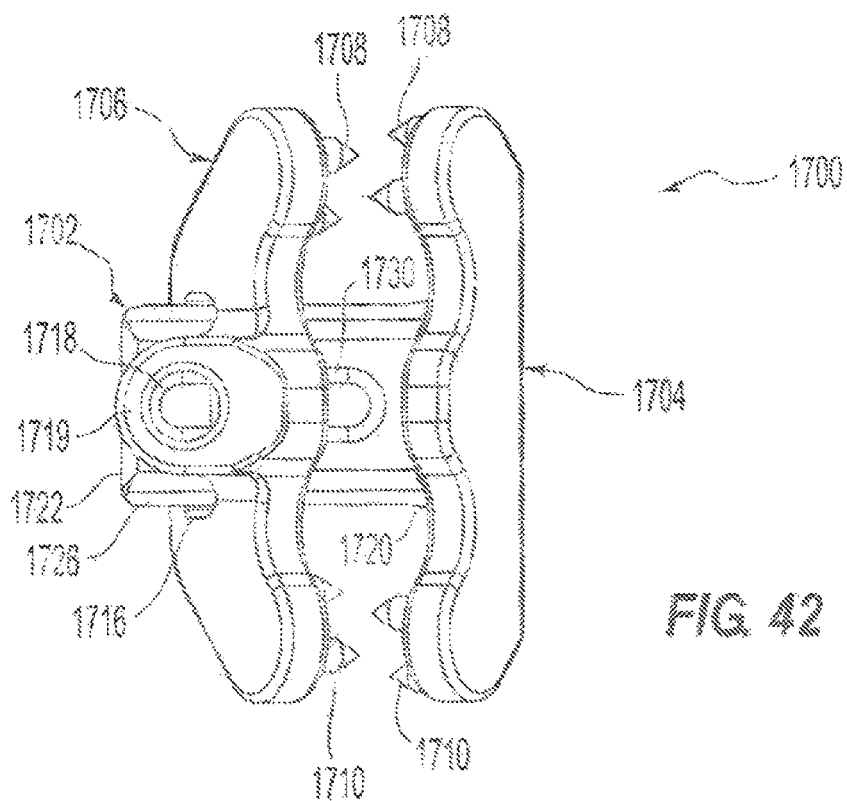
FIG. 42 is an elevation view of the posterior side of the interspinous implant of FIG. 41.
Figure 43:
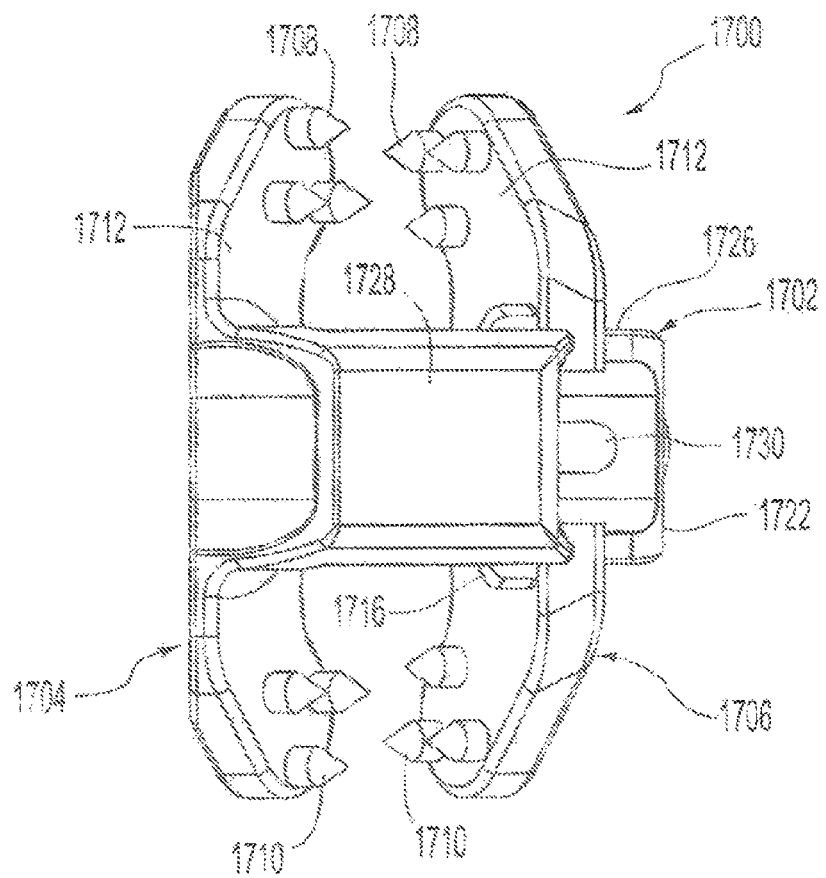
FIG. 43 is an elevation view of an anterior side of the interspinous implant of FIG. 41.

The second extension 1706 also may include a spacer aperture 1716 sized to receive a portion of the spacer 1702. In one example, the spacer aperture 1716 is sized to receive the first sidewall portion 1726. The spacer aperture 1716 may be sized to permit or limit relative lateral or rotational movement between the second extension 1706 and the spacer 1702 when the interspinous implant 1700 is assembled as shown in FIGS. 42-44.

Referring now to FIGS. 45-49B, another example interspinous implant 1800 is shown and described including a spacer 1802, a first extension or plate 1804, and a second extension or plate 1806. The spacer 1802 may be permanently or adjustably connected to either or both of the first and second extensions 1804, 1806. In at least one example, the spacer 1802 is permanently connected to the first extension 1804 and adjustably connected to the second extension 1806. In at least one example, the first extension 1804 is integrally formed as a single piece with the spacer 1802, and the second extension 1806 is a separate piece axially moveable along a longitudinal axis 1824 (FIG. 48) over a length of the spacer 1802.

The spacer 1802 may include first and second ends 1820, 1822 that are spaced apart along the longitudinal axis 1824 such that first end 1820 is proximate first extension 1804 and second end 1822 is distal first extension 1804. The spacer 1802 may further include first and second sidewall portions 1826, 1828, that each may include one or more bores or through holes 1830. The first and second sidewall portions 1826, 1828 may be divided by one or more slots or cutouts such as superior and inferior slots 1832, 1834.

The first sidewall portion 1826 has a length $X_1$ measured from the contact surface 1812 of the first extension 1804, and the second sidewall portion has a length $X_2$ measured from the contact surface 1812 of the first extension 1804. In this embodiment, the length $X_1$ is less than the length $X_2$. In other embodiments, such as the interspinous implant 1700 shown in FIGS. 41-44, the first sidewall portion 1726 has a length that is greater than a length of the second sidewall portion 1728. The length of the second sidewall portion may be provided to clear the facets.

Figure 48:
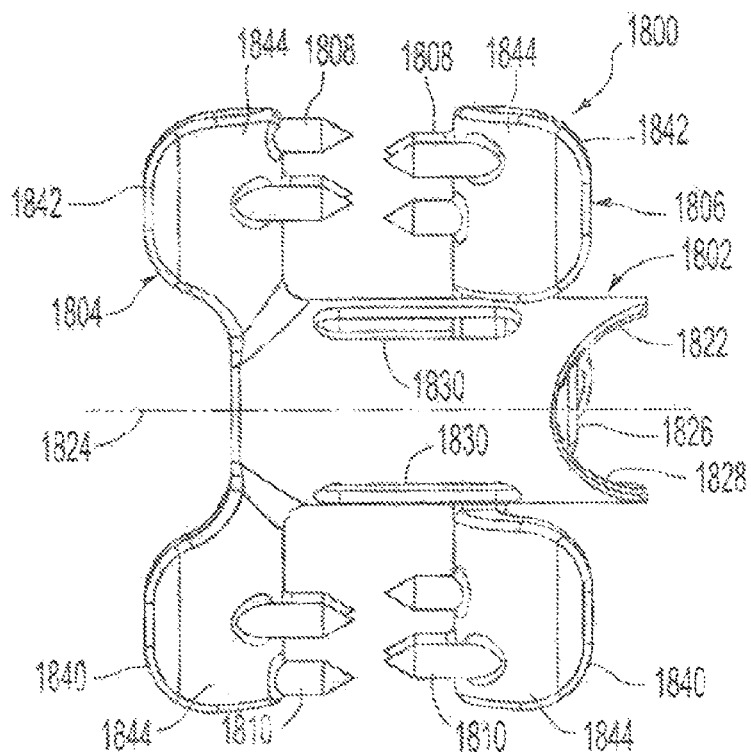
FIG. 48 is an elevation view of an anterior side of the interspinous implant of FIG. 47.
Figure 49A:
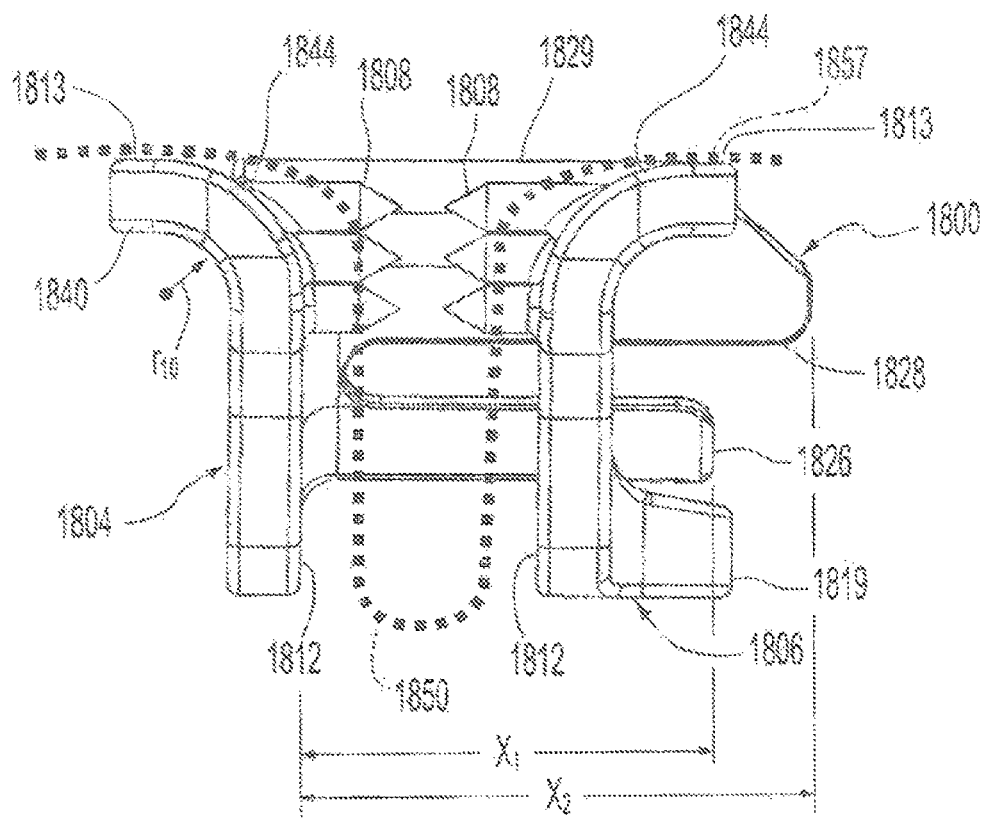
FIG. 49A is a top view of the interspinous implant of FIG. 47 showing engagement of the implant with a relatively flat spinous process.

The first and second extensions 1804, 1806 may extend in both superior and inferior directions from the spacer 1802. Each of the first and second extensions 1804, 1806 may include first and second sets of fasteners 1808, 1810, such as spikes, pins, screws, nail, etc. that extend from a contact surface 1812. The first and second extensions 1804, 1806 may further include a flared portion 1840, 1842 at opposite ends thereof that define a curved surface or curvature 1844 (FIG. 48). The curved surface 1844 may be part of the contact surface 1812 or may be a continuous curvature with the contact surface 1812. The first and second sets of fasteners 1808, 1810 may extend from the contact surface 1812 and the curved surface 1844. As shown in the embodiments the fasteners 1808, 1810 may variable lengths as shown in FIG. 49A. For example, they may extend further in order for the fastener ends to reside in a plane defined by the fastener ends. In at least one example, the first and second sets of fasteners 1808, 1810 are arranged generally parallel with each other and may, in some arrangements, be arranged collinear or offset with fasteners on the opposing extension 1804, 1806. Moreover, fasteners 1808, 1810 may extend perpendicular to the tangent of curved surface 1844 such that some of the fasteners diverge as they extend from contact surfaces 1812 and/or curved surface 1844.

Figure 49B:
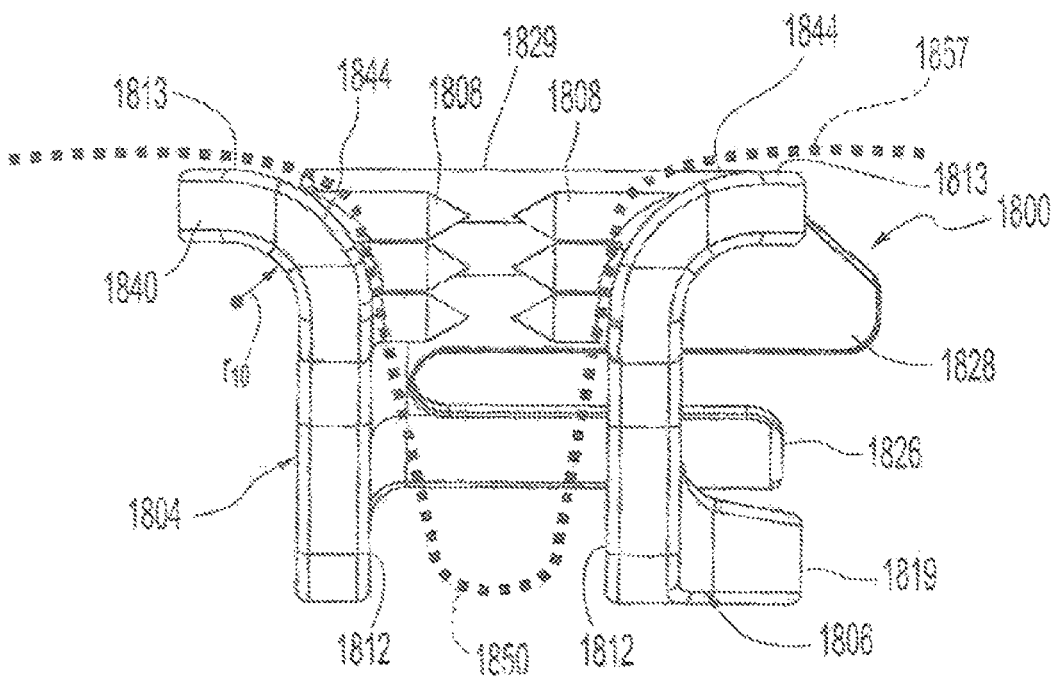
FIG. 49B is a top view of the interspinous implant of FIG. 47 showing engagement of the implant with a relatively flared spinous process.

The curved surface 1844 may extend in an arch or curve with a constant radius $r_{10}$. The radius $r_{10}$ may increase or decrease moving along the flared portions 1840, 1842. The curved surface 1844 is a bent or flared surface in the anterior direction. The use of flared portions 1840, 1842 enhance the ability of the first and second sets of fasteners 1808, 1810 to seat in spinous processes having various geometries. For example, in a spinous process 1850 with little or no flare (i.e., a spinous process presents essentially a flat, vertical bone surface), the first and second sets of fasteners 1808, 1810 penetrate and bite into the bone as shown in FIG. 49A. In a spinous process 1850 with a larger amount of flare (i.e., the spinous processes are wedge shaped or curved), the flared portions 1840, 1842 allow the first and second sets of fasteners 1808, 1810 to bite into the bone without interference from the anterior portions of the first and second extensions 1804, 1806 abutting the bone and limiting penetration as shown in FIG. 49B. The flared portions 1840, 1842 also permit the first and second extensions 1804, 1806 to lie close to the lamina 1857 to help initially position the first and second extensions 1804, 1806 and increase a bio-mechanical interlock of the interspinous implant 1800 with the bone. Additionally, if the fasteners 1808, 1810 are arranged to extend perpendicular to the tangent of the flared portions 1840, 1842 the fasteners would penetrate into the lamina 1857.

The second extension 1806 may include a spacer aperture 1816 sized to receive a portion of the spacer 1802, such as, for example, the first sidewall portion 1826. The second extension 1806 also may include a mounting portion 1819 having a set screw bore 1818 defined therein. The set screw bore 1818 may be sized to receive fasteners such as a threaded set screw that extends through the set screw bore 1818 and contacts a portion of the spacer 1802, such as first sidewall portion 1826, to secure the second extension 1806 in a fixed axial position relative to the spacer 1802 and first extension 1804. To facilitate a set screw engaging with first sidewall portion 1826, the posterior facing surface of first sidewall portion 1826 may have surface texture, such as striations, knurling, or the like.

Figure 50:
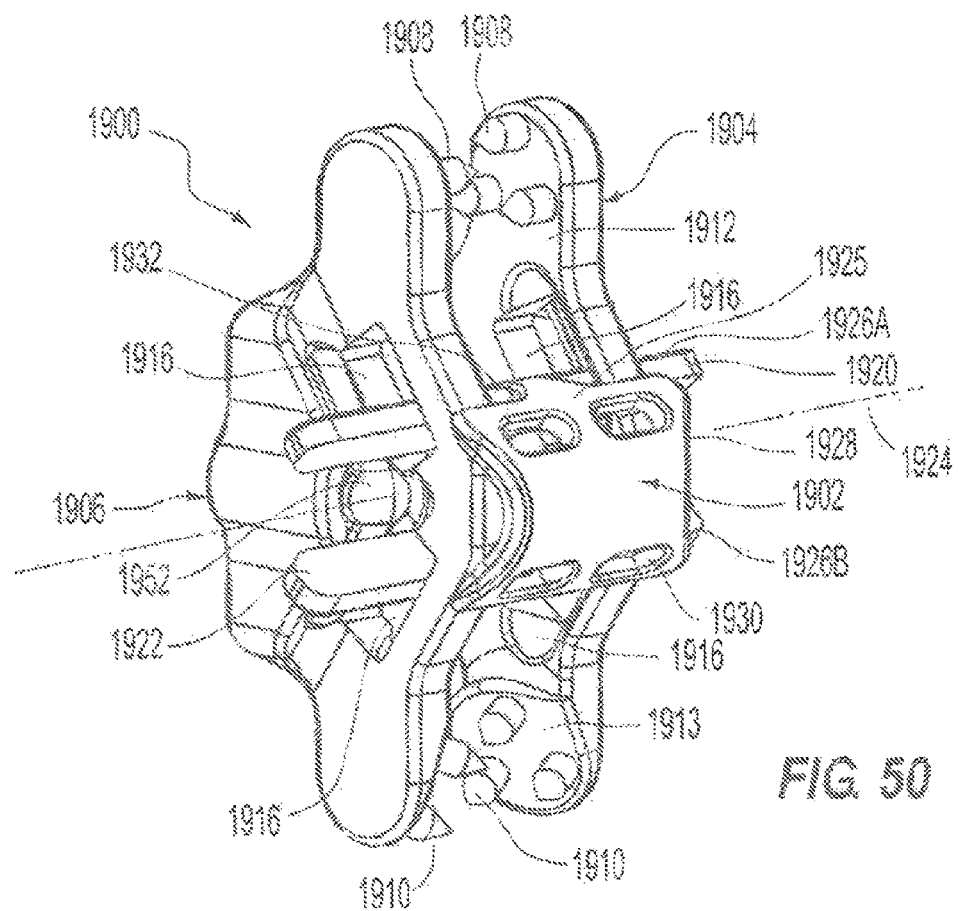
FIG. 50 is a perspective view of another example interspinous implant of the present invention.
Figure 51:
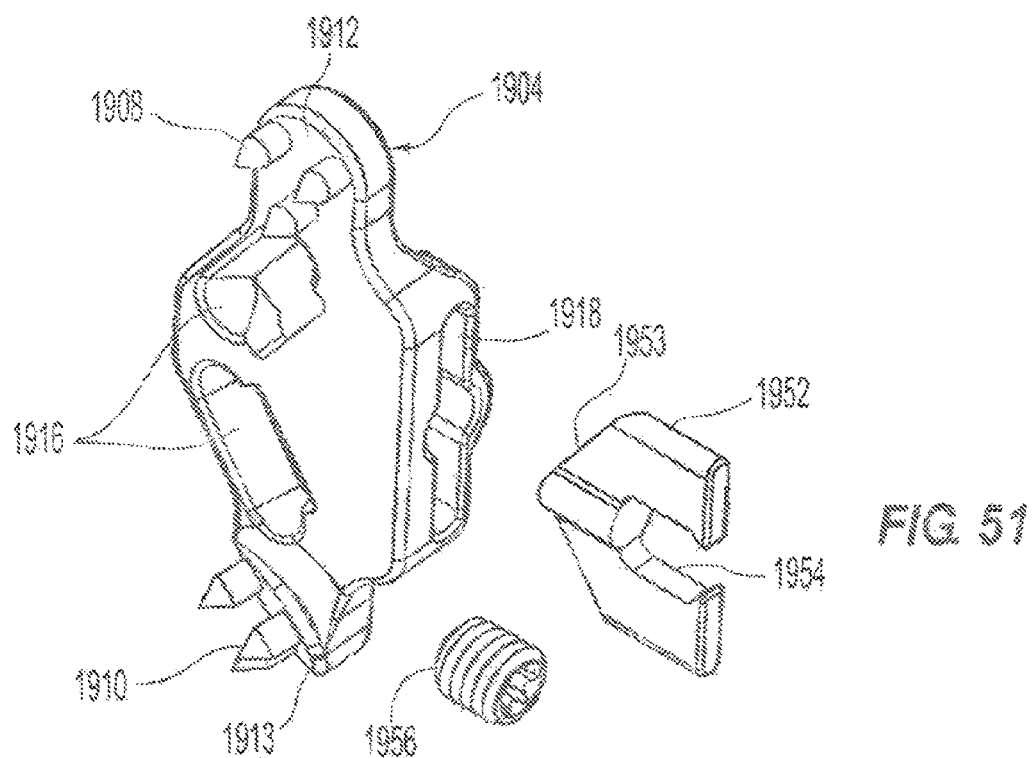
FIG. 51 is an exploded perspective view of a portion of the interspinous implant of FIG. 50.
Figure 52:
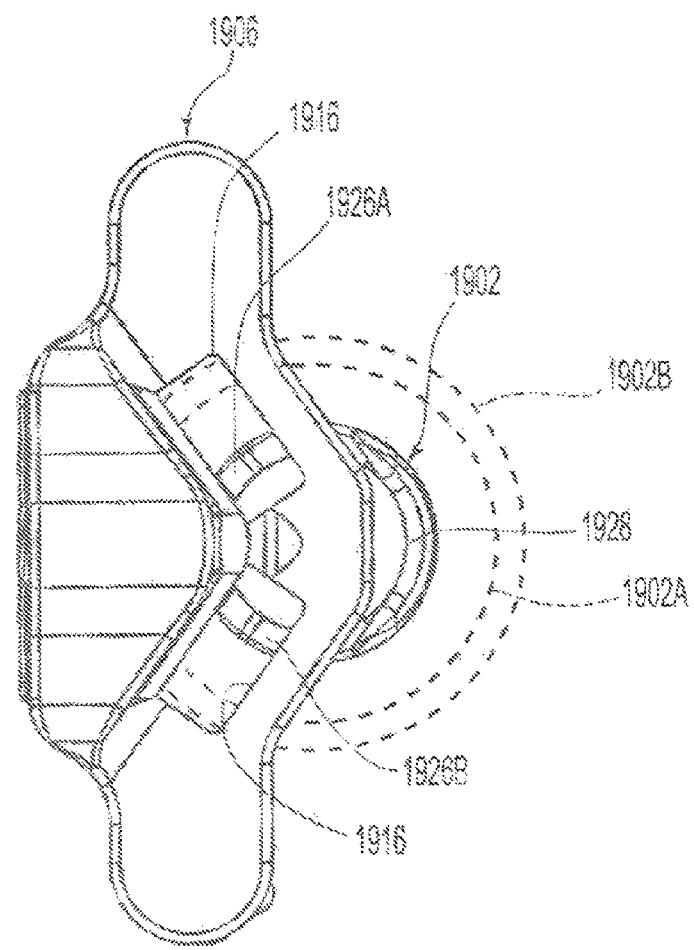
FIG. 52 is a lateral elevation view of the interspinous implant of FIG. 50.

Referring now to FIGS. 50-52, another example interspinous implant 1900 is shown having a spacer 1902, a first extension or plate 1904 and a second extension or plate 1906. In this example, the spacer 1902 is formed as a separate piece from the first and second extensions 1904, 1906 to provide a modular construction for the interspinous implant 1900. The spacer 1902, and first and second extensions 1904, 1906 may be provided in various sizes and shapes that may be combined interoperatively to achieve a desired fit with a patient's anatomy. For example, the same first and second extensions 1904, 1906 may be used with different sizes of spacers 1902, 1902A, 1902B as shown in FIG. 52.

The spacer 1902 and first and second extensions 1904, 1906 may comprise different materials such as polymers and metals as previously identified herein. In one example, the first and second extensions 1904, 1906 may comprise a metal material and the spacer 1902 may be comprise a polymer material. Spacer 1902 may be radiolucent to facilitate, for example, visualization with medical imaging.

The spacer 1902 may comprise first and second ends 1920, 1922 spaced apart along a longitudinal axis 1924. The spacer 1902 includes a first sidewall portion 1926A, 1926B and a second sidewall portion 1928. The sidewall portions 1926A, 1926B and 1928 may be connected along the longitudinal axis 1924 by transverse wall portions 1925 and separated or be divided from each other with one or more dividing slots 1932. The first sidewall portions 1926A, 1926B may be sized to extend through apertures 1916 in the first and second extensions 1904, 1906 to provide an adjustable connection there between as explained further below. Also, spacer 1902 may have channels or through holes 1930.

Figure 54:
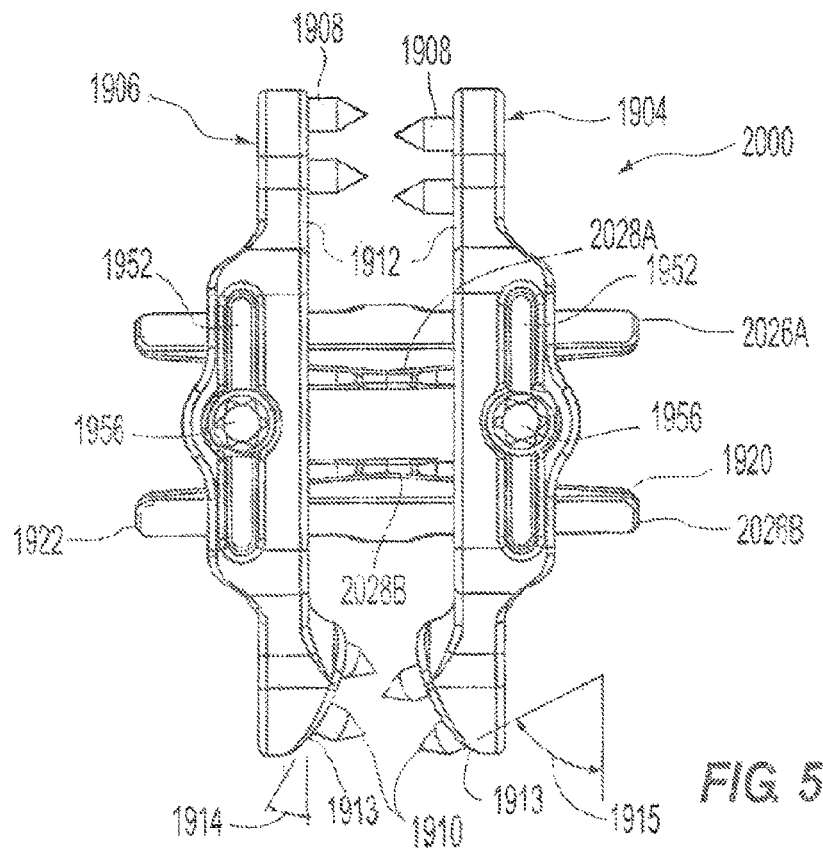
FIG. 54 is an elevation view of a posterior side of the interspinous implant of FIG. 54.

The first and second extensions 1904, 1906 extend in superior and inferior directions from the spacer 1902. Each of the first and second extensions 1904, 1906 may include first and second sets of fasteners 1908, 1910 that extend from first and second contact surfaces 1912, 1913. The first contact surface 1912 may be arranged generally perpendicular to the longitudinal axis 1924 of the spacer 1902. The second contact surface 1913 may be arranged at a compound angle or other angled relationship relative to the longitudinal axis 1924. For example, the second contact surface 1913 may be a compound angle that angles inferiorly and anteriorly as shown in FIG. 54, which may make interspinous implant 1900 particularly suited for L5-S1.

The first and second sets of fasteners 1908, 1910 may extend generally perpendicular to the first and second contact surfaces 1912, 1913, respectively. In the illustrated example, the first sets of fasteners 1908 may be arranged generally parallel, whether aligned or offset, with each other on the first and second extensions 1904, 1906. The second sets of fasteners 1910 may be arranged at a non-parallel angle relative to each other on the first and second extensions 1904, 1906 as shown in at least FIG. 54. The first set of fasteners 1908 may extend perpendicular to the plane defined by first contact surfaces 1912. The second set of fasteners 1910 is arranged at an angle 1915 relative to the plane defined by the first contact surface 1912 as shown in FIG. 54.

The first and second extensions 1904, 1906 also may include the spacer aperture 1916 sized to receive a portion of the sidewall portions 1926A, 1926B and 1928 of the spacer 1902. FIG. 50 illustrates the first sidewall portions 1926A, 1926B extending through spacer apertures 1916 of each of the first and second extensions 1904, 1906. The spacer apertures 1916 may be sized greater than the size of the first sidewall portions 1926A, 1926B to permit some relative lateral and rotational movement of the spacer 1902 in addition to relative axial movement along the longitudinal axis 1924 of the spacer 1902.

The first and second extensions 1904, 1906 may further include a bore 1918 sized to receive a locking block 1952. The locking block 1952 may be arranged to releasably contact the first sidewall portions 1926A, 1926B of the spacer 1902 to secure the first and second extensions 1904, 1906 in a fixed axial position relative to the spacer 1902. The locking block 1952 may include a mating surface 1953 at a distal end thereof, a set screw cutout 1954 at a proximal end thereof, and a set screw 1956 sized to fit within the set screw cutout 1954. The bore 1918 may include threads that threadably engage the threads of the set screw 1956. Rotation of the set screw 1956 may advance the mating surface 1953 distally into contact with the first sidewall portions 1926A, 1926B.

The spacer apertures 1916 may be arranged noncollinearaly and be open to bore 1918. The mating surface 1953 of the locking block 1952 may be angled such that the mating surface 1953 extends into spacer apertures 1916 to trap the first sidewall portions 1926A, 1926B in a self-centering relationship within the spacer apertures 1916. In an alternative arrangement, the spacer apertures 1916 are collinear and the mating surface 1953 of the locking block 1952 is generally planer across its width so that the spacer 1902 is both vertically and axially adjustable relative to the first and second extensions 1904, 1906 by moving the first sidewall portions 1926A, 1926B within the spacer apertures 1916 before clamping them into place with the locking block 1952.

Figure 53:
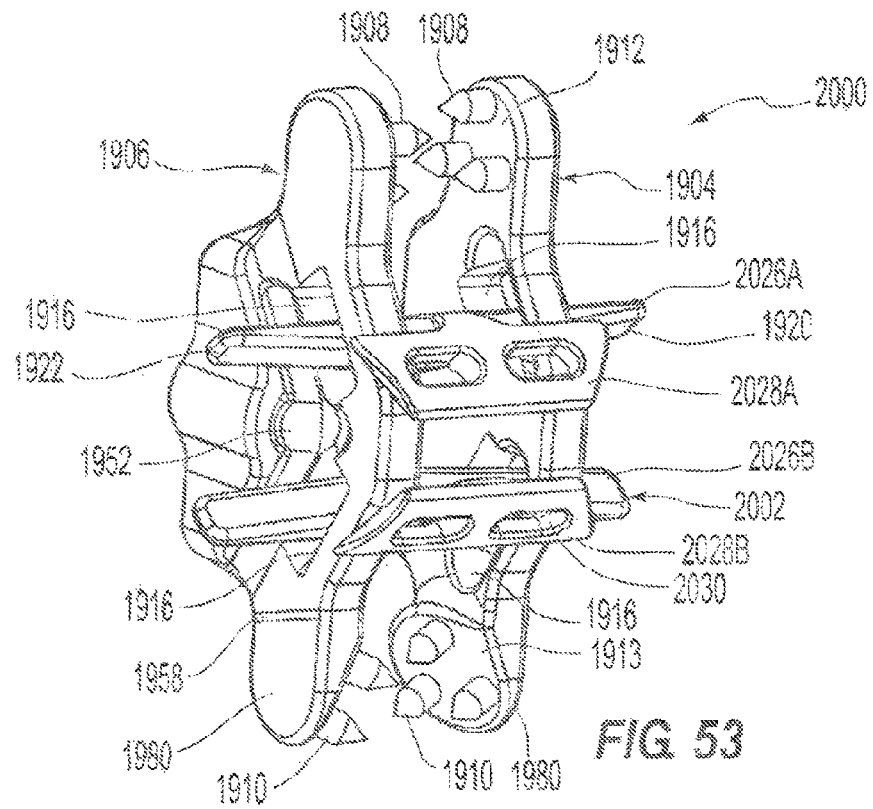
FIG. 53 is a perspective view of another example interspinous implant of the present invention.

Referring now to FIGS. 53-54, another example interspinous implant 2000 is shown having a spacer 2002 and the first and second extensions or plates 1904, 1906 described above with reference to FIGS. 50-52. The spacer 2002 may be separated into two separate halves, wherein a first half includes a first sidewall portion 2026A and a second sidewall portion 2028A, and a second half includes a first sidewall portion 2026B and a second sidewall portion 2028B. The spacer 2002 may include at least one slot 2030 defined therein.

The first sidewall portions 2026A, 2026B may be sized to extend through spacer apertures 1916 in the first and second extensions 1904, 1906. The locking block 1952 secures the arms of the spacer 2002 to the first and second extensions 1904, 1906 as described above with reference to the interspinous implant 1900. The independent halves of the spacer 2002 may be individually adjusted vertically, laterally, and angularly relative to the first and second extensions 1904, 1906 to vary the position and height of the spacer 2002. In one example, after a loosely assembled interspinous implant 2000 is placed with the spacer 2002 between adjacent spinous processes, a distraction tool may be engaged with the halves of the spacer 2002 and activated to separate the halves of the spacer 2002 and space the spinous processes to a desired spacing. The locking block 1952 may then be used to secure that spacing.

Alternatively, the spacer apertures 1916 and locking block 1952 may be arranged such that advancement of the locking block 1952 by rotating the set screw 1956 wedges the halves of the spacer 2002 apart.

The portions of the first and second extensions 1904, 1906 that define the second contact surface 1913 may be defined as an inferior fastener pad 1980 that carry the second sets of fasteners 1910. The fastener pads 1980 may be rotated about a sacral inclination axis such that the fastener pads 1980 form a compound angle flared inferiorly and rotated anteriorly. This compound angle may be particularly suitable for gripping an S1 vertebrae.

The orientation of the fastener pad 1980 may be fixed or it may be adjustable. Adjustability may be provided by incorporating a bend zone 1958 (see FIG. 53). The bend zone 1958 may be defined by providing a thinner, relatively easy to bend portion of the first and second extensions 1904, 1906. Adjustability also may be provided by incorporating a joint (not shown) such as a hinge, ball-and-socket, pivot or other suitable joint at a connection point of the fastener pad 1980 to the remaining portions of the first and second extensions 1904, 1906. The joint may be adjustable between unlocked and locked positions, wherein in an unlocked position the second set of fasteners 1910 may be penetrated into the bone to stabilize the joint. The joint may be locked using, for example, a set screw to fix an orientation of the fastener pad 1980 once it has been established relative to the remaining portions of the first and second extensions 1904, 1906.

Figure 55:
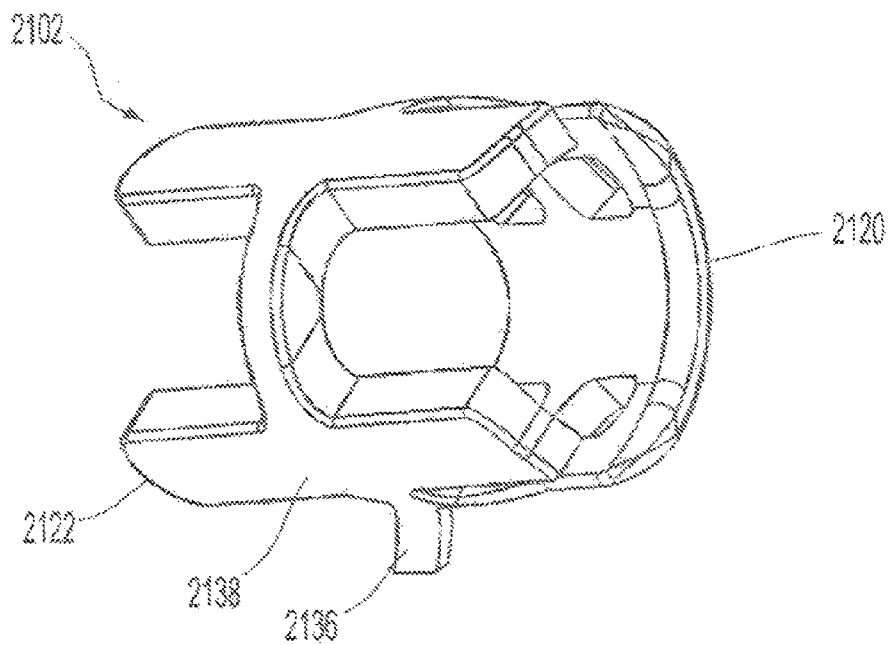
FIG. 55 is a perspective view of an example spacer of an interspinous implant of the present invention.
Figure 56:
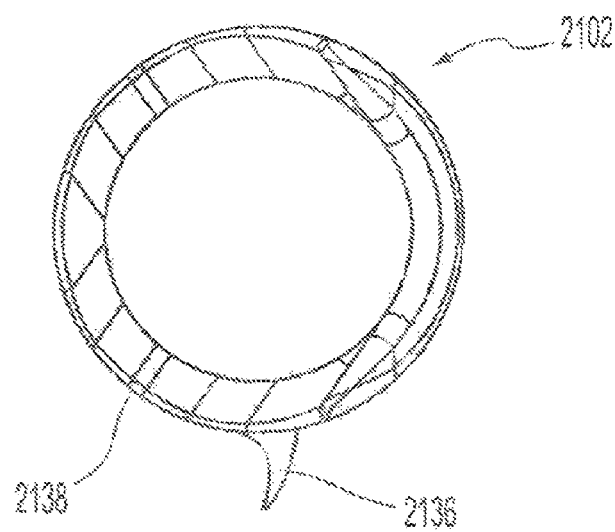
FIG. 56 is a lateral elevation view of the spacer of FIG. 55.

Referring now to FIGS. 55-56, an alternative spacer configuration 2102 is shown. The spacer 2102 may include one or more hook features 2136 extending from an outer surface 2138. The hook feature 2136 may extend in any direction and may have any shape and size. The hook feature 2136 may be operable to bite into an adjacent bone or hook behind an adjacent bone, such as a spinous process or lamina to help in securing the spacer 2102 to the spinous process.

FIGS. 55-56 illustrate the hook feature 2136 extending inferiorly and curved posteriorly. This arrangement of the hook feature 2136 may be well adapted for hooking onto a superior edge of any vertebrae and, in particular, the S1 vertebrae. The spacer 2102 may be combined with any of the first and second extensions of the various implants described herein. The hook feature 2136 may be well suited for combination with an interspinous implant that is specifically adapted for fixation to the L5 and S1 vertebrae. In certain aspects, the hook feature 2136 may be provided with any of the aforementioned spacers. When used in conjunction with the S1 vertebrae, the inferior portions of the first and/or second extensions, lobes, or plates may be reduced or even eliminated.

Figure 57:
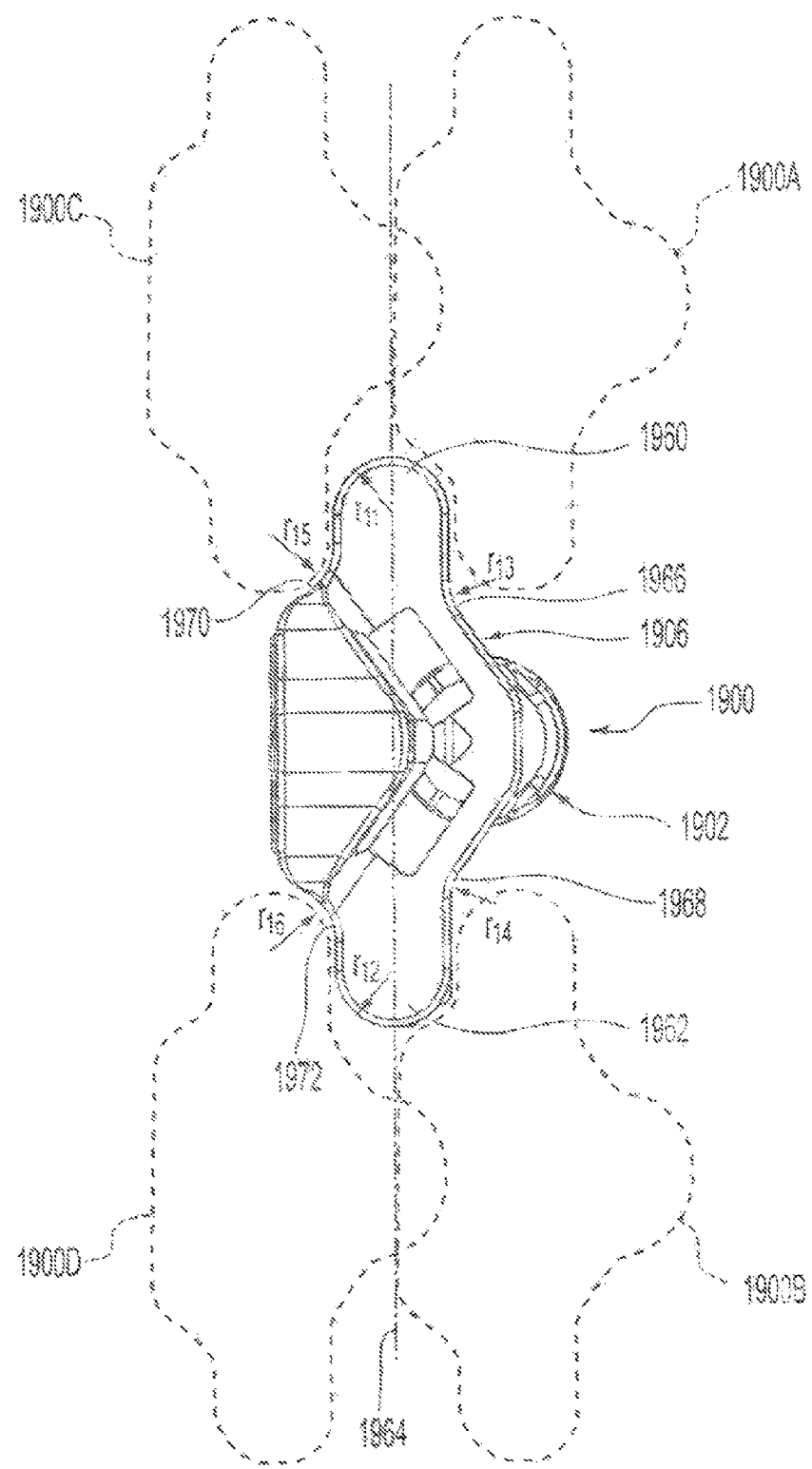
FIG. 57 is a lateral elevation view of the interspinous implant of FIG. 50 showing possible interfitting of multiple implants at multiple levels.
Figure 58:
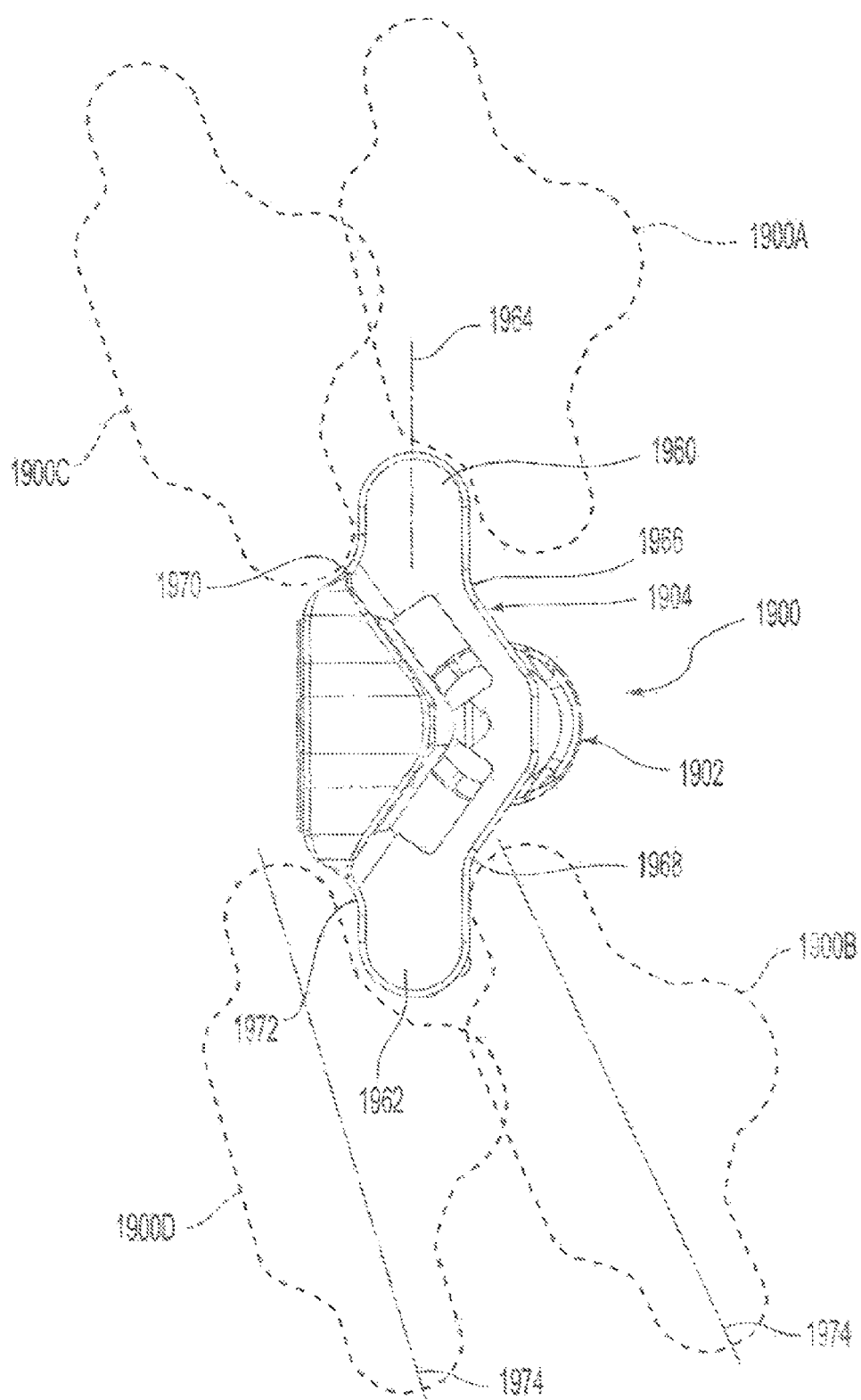
FIG. 58 is a lateral elevation view of the interspinous implant of FIG. 50 showing additional possible interfitting of implants at multiple levels.

Referring now to FIGS. 57-58, the interspinous implant 1900 is shown and described in further detail. At least one of first and second extensions 1904, 1906 may include first and second lobes 1960, 1962 at opposing ends thereof (second extension 1906 being shown in FIGS. 57-58). The lobes have a peripheral surface with a radius $r_{11}$, $r_{12}$, respectively. A centerline 1964 extends from the first lobe 1960 to the second lobe 1962.

The second extensions 1906 further includes a first concave surfaces 1966, 1968 having a radius $r_{13}$, $r_{14}$, respectively, along one side surface, and a pair of second concave surfaces 1970, 1972 having a radius $r_{15}$, $r_{16}$, respectively, along an opposing side surface. The radiuses $r_{13}$, $r_{14}$, $r_{15}$, $r_{16}$ may be similar in size to the radiuses $r_{11}$, $r_{12}$. For example, the radiuses $r_{13}$, $r_{14}$, $r_{15}$, $r_{16}$ may be within about 5% to about 30% greater or less than the radiuses $r_{11}$, $r_{12}$. The first extension 1904 would have similar dimensions, but is not shown for convenience.

The first lobe 1960 may be referred to as a superior lobe that is anteriorly adjacent to the first concave surface 1966 and posteriorly adjacent to the concave surface 1970. The second lobe 1962 may be referred to as an inferior lobe that is anteriorly adjacent to a first concave surface 1968 and posteriorly adjacent to a second concave surface 1972. The radiuses of the first and second lobes 1960, 1962 may be similar such that when two interspinous implants 1900 are placed at adjacent spinal levels, the first and second lobes 1960, 1962 are interchangeably interfittable with adjacent concave surfaces 1966, 1968, 1970, 1972. Depending on patient anatomy and other surgical considerations, an interspinous implant 1900 may be interfit anteriorly or posteriorly with a first or second lobe 1960, 1962 in any combination as shown with the plurality of interspinous implants 1900 and 1900A-1900D shown in FIG. 57. Furthermore, the interspinous implant 1900 may be angled anteriorly or posteriorly while maintaining the interfitting relationship as shown in FIG. 58, wherein an angled centerline 1974 of the interspinous implants 1900A-1900D is arranged at an angle relative to the centerline 1964.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

We claim:

1. An implant for placement between spinous processes of adjacent vertebrae of a spine, the implant comprising:
    a spacer having a longitudinal axis operable to abut the spinous processes and maintain the spinous processes in a spaced apart relationship corresponding to a predetermined minimum spacing between the spinous processes, the spacer comprising first and second members having a gap therebetween, the first and second members each having a total surface area, the total surface area of the first member greater than the total surface area of the second member;
    a first extension forming a plane projecting from the spacer transverse to the longitudinal axis to lie generally alongside first lateral sides of the spinous processes of adjacent vertebrae;
    first and second fasteners moveably coupled to the first extension and adapted to engage the first lateral sides of the spinous processes to limit the maximum spacing between the spinous processes, wherein the movement of the first and second fasteners allows angular adjustment between the first extension and the first and second fasteners over a plurality of angles;
    a second extension forming a second plane projecting from the spacer transverse to the longitudinal axis to lie generally alongside second lateral sides of the spinous processes of adjacent vertebrae, the second extension translatably coupled to the spacer for translation along the longitudinal axis; and
    at least a third fastener coupled to the second extension and adapted to engage at least one of the second lateral sides of the spinous processes to limit the maximum spacing between the spinous processes.

2. The implant of claim 1, wherein at least one of the plurality of angles is 90°.

3. The implant of claim 1, wherein the first and second fasteners are removably coupled to the first extension.

4. The implant of claim 1, wherein the first extension comprises first and second sockets and wherein the first and second fasteners each comprise a ball that cooperatively engages the sockets to allow for the angular adjustment.

5. The implant of claim 4, wherein the ball and socket provide for rotational and pivotal movement to allow for the angular adjustment.

6. The implant of claim 1, wherein the first fastener comprises a plurality of fasteners coupled to a base.

7. The implant of claim 6, wherein the base allows for angular adjustment of the plurality of fasteners simultaneously.

8. The implant of claim 1, wherein the third fastener is moveably coupled to the second extension, and wherein the movement of the third fastener allows angular adjustment between the second extension and the third fastener over a plurality of angles.

9. The implant of claim 8, wherein the second extension comprises an aperture shaped to cooperatively engage and translate over the spacer.

10. The implant of claim 1, wherein movement of the first and second fasteners varies the first and second fasteners distance from the first extension.

11. The implant of claim 1, wherein the first and second fasteners are adapted to be angulated to a desired angle position relative to the first extension, and are adapted to be locked into the desired angle position.

12. An implant for placement between spinous processes of adjacent vertebrae of a spine, the implant comprising:
    a spacer comprising first and second members having a gap therebetween, the first and second members extending from a first end to a second end along a longitudinal axis and each having a total surface area, the total surface area of the first member greater than the total surface area of the second member, the spacer having a sidewall generally parallel to the longitudinal axis and having superior and inferior surfaces operable to abut the spinous processes and maintain the spinous processes in a spaced apart relationship, the superior and inferior surfaces being spaced apart a distance corresponding to a predetermined minimum spacing between the spinous processes;
    a first extension forming a first plane projecting from the spacer transverse to the longitudinal axis to lie generally alongside the spinous processes of adjacent vertebrae;
    a second extension forming a second plane projecting from the spacer transverse to the longitudinal axis to lie generally alongside the spinous processes of adjacent vertebrae;
    an aperture formed in the second extension, the aperture shaped to cooperatively engage the spacer such that the second extension translates over the spacer; and
    at least a first fastener moveably coupled to at least one of the first or second extensions and extending from the corresponding first plane or second plane formed by the first or second extension to which the first fastener is attached and adapted to engage at least one of the spinous processes to limit the maximum spacing between the spinous processes, wherein the movement of the first fastener allows angular adjustment between the extension to which it is attached and the first fastener over a plurality of angles.

13. The implant of claim 12, wherein the first plane and the second plane are parallel.

14. The implant of claim 12, wherein the first plane and the second plane are angled with respect to each other.

15. The implant of claim 12, wherein the spacer comprises at least one opening in the superior surface, at least one opening in the inferior surface, and at least one transverse passageway extending from the opening in the superior surface to the opening in the inferior surface to allow bone growth through the spacer.

16. The implant of claim 15, wherein the transverse passageway is formed by a hollow cavity formed by the sidewalls of the spacer.

17. A method of treating spine disease comprising:
providing an implant, comprising,
a spacer with a longitudinal axis, the spacer operable to abut adjacent spinous processes and maintain the adjacent spinous processes in a spaced apart relationship corresponding to a predetermined minimum spacing between the adjacent spinous processes, the spacer comprising first and second members having a gap therebetween, the first and second members each having a total surface area, the total surface area of the first member greater than the total surface area of the second member;
a first extension forming a plane projecting from the spacer transverse to the longitudinal axis to lie generally alongside first lateral surfaces of the adjacent spinous processes; and
first and second fasteners moveably coupled to the first extension and adapted to engage the first lateral surfaces of the adjacent spinous processes to limit the maximum spacing therebetween, wherein the movement of the first and second fasteners allows angular adjustment between the first extension and the first and second fasteners over a plurality of angles;
inserting the implant between spinous processes of adjacent vertebrae; and
angling the first and second fasteners with respect to the plane such that the first and second fasteners bite into the adjacent spinous processes;
translating a second extension towards the first extension along the longitudinal axis until the second extension engages at least one of the spinous processes;
wherein the implant provides both an extension stop and a flexion stop when the first and second fasteners bite into the adjacent spinous processes.

18. The method of claim 17, further comprising:
angling a third fastener associated with the second extension such that the third fastener is adapted to engage at least one of the adjacent spinous processes.

19. An implant for placement between spinous processes of adjacent vertebrae of a spine, the implant comprising:
a spacer adapted to contact an inferior surface of a superior spinous process and a superior surface of an inferior spinous process when placed therebetween, the spacer comprising first and second members having a gap therebetween, the first and second members each having a total surface area, the total surface area of the first member greater than the total surface area of the second member;
a first extension forming a plane projecting from the spacer, the first extension adapted to lie generally alongside a first lateral side of the superior and inferior spinous processes;
a second extension forming a second plane and moveably coupled to the first extension, the second extension adapted to lie generally alongside a second lateral side of the superior and inferior spinous processes;
first and second fasteners coupled to the first extension and adapted to bite into the first lateral sides of the superior and inferior spinous processes to couple the first extension thereto; and
wherein the second extension and spacer are adapted to translate along a longitudinal axis when the second extension is moveably coupled to the first extension.

20. The implant as in claim 19, further comprising third and fourth fasteners coupled to the second extension and adapted to bite into the second lateral sides of the superior and inferior spinous processes to couple the second extension thereto.

21. The implant as in claim 20, wherein the third and fourth fasteners are adapted to be positioned at a plurality of angles relative to the spacer when the second extension is moved relative to the spacer.

22. The implant as in claim 19, wherein the first and second fasteners moveably coupled to the first extension, wherein the movement of the first and second fasteners allows angular adjustment between the first extension and the first and second fasteners over a plurality of angles.

23. The implant as in claim 19, wherein the second extension is adapted to be at least partially disposed in the gap when the second extension is moved relative to the spacer.

24. The implant as in claim 19, wherein the first member is coupled to an anterior portion of the first extension and the second member is coupled to a posterior portion of the first extension when the spacer is disposed between the superior and inferior spinous processes.

25. An implant for coupling to spinous processes of adjacent vertebrae of a spine, the implant comprising:
a first plate member forming a first plane adapted to lie generally alongside a first lateral side of superior and inferior spinous processes;
a second plate member forming a second plane and moveably coupled to the first plate member, the second plate member adapted to lie generally alongside a second lateral side of the superior and inferior spinous processes;
a spacer disposed between the first and second plate members, the spacer including a longitudinal axis extending from the first plate member to the second plate member, the spacer comprising first and second members having a gap therebetween, the first and second members each having a total surface area, the total surface area of the first member greater than the total surface area of the second member; and
first and second fasteners movably coupled to the first plate member and adapted to bite into the first lateral sides of the superior and inferior spinous processes to couple the first plate member thereto, wherein the movement of the first and second fasteners allows angular adjustment between the first plate member and the first and second fasteners over a plurality of angles,
wherein the second plate member is translatably coupled to the spacer for translation along the longitudinal axis.

26. The implant of claim 25, wherein the spacer extends from the first plate member for moveably coupling the first plate member with the second plate member.

27. The implant of claim 26, wherein the spacer is adapted to engage an inferior surface of the superior spinous process and a superior surface of the inferior spinous process when disposed therebetween.

28. The implant of claim 25, further comprising third and fourth fasteners moveably coupled to the second plate member and adapted to bit into the second lateral sides of the superior and inferior spinous processes to couple the second plate member thereto, wherein the movement of the third and fourth fasteners allows angular adjustment between the second plate member and the third and fourth fasteners over a plurality of angles.

\* \* \* \* \*

UNITED STATES PATENT AND TRADEMARK OFFICE
CERTIFICATE OF CORRECTION

| | | |
|---|---|---|
| PATENT NO. | : 9,265,532 B2 | Page 1 of 1 |
| APPLICATION NO. | : 12/854125 | |
| DATED | : February 23, 2016 | |
| INVENTOR(S) | : Lamborne et al. | |

It is certified that error appears in the above-identified patent and that said Letters Patent is hereby corrected as shown below:

In the Claims

In column 30, line 19, in Claim 22, after "fasteners", insert --are--, therefor

Signed and Sealed this
Sixteenth Day of August, 2016

Michelle K. Lee
*Director of the United States Patent and Trademark Office*